(12) United States Patent
Saxonov et al.

(10) Patent No.: US 9,222,128 B2
(45) Date of Patent: Dec. 29, 2015

(54) MULTIPLEXED DIGITAL ASSAYS WITH COMBINATORIAL USE OF SIGNALS

(75) Inventors: Serge Saxonov, Oakland, CA (US); Simant Dube, Pleasanton, CA (US); Benjamin J. Hindson, Livermore, CA (US); Adam M. McCoy, Davis, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 345 days.

(21) Appl. No.: 13/424,304

(22) Filed: Mar. 19, 2012

(65) Prior Publication Data
US 2012/0329664 A1    Dec. 27, 2012

Related U.S. Application Data

(60) Provisional application No. 61/454,373, filed on Mar. 18, 2011.

(51) Int. Cl.
| | | |
|---|---|---|
| G01N 33/48 | (2006.01) | |
| G01N 33/50 | (2006.01) | |
| G01N 31/00 | (2006.01) | |
| C12Q 1/68 | (2006.01) | |
| G06F 19/20 | (2011.01) | |
| G06F 19/12 | (2011.01) | |
| G06F 19/18 | (2011.01) | |
| G06F 17/10 | (2006.01) | |
| G06F 17/12 | (2006.01) | |
| G06F 17/11 | (2006.01) | |

(52) U.S. Cl.
CPC .............. *C12Q 1/6851* (2013.01); *G06F 19/12* (2013.01); *G06F 19/18* (2013.01); *G06F 19/20* (2013.01); *G06F 17/10* (2013.01); *G06F 17/11* (2013.01); *G06F 17/12* (2013.01)

(58) Field of Classification Search
None
See application file for complete search history.

(56) References Cited

U.S. PATENT DOCUMENTS

| | | |
|---|---|---|
| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |
| 5,176,203 A | 1/1993 | Larzul |
| 5,225,332 A | 7/1993 | Weaver et al. |
| 5,270,183 A | 12/1993 | Corbett et al. |

(Continued)

FOREIGN PATENT DOCUMENTS

| | | |
|---|---|---|
| EP | 1 522 582 A2 | 4/2005 |
| EP | 1 522 582 B1 | 4/2007 |

(Continued)

OTHER PUBLICATIONS

Dube et al. Mathematical Analysis of copy number Variation in a DNA Sample Using Digital PCR on a Nanofluidic Device (2008) PLoS ONE 3(8): e2876. doi:10.1371/journal.pone.0002876.

(Continued)

*Primary Examiner* — Russell S Negin
(74) *Attorney, Agent, or Firm* — Kolisch Hartwell, P.C.

(57) ABSTRACT

System, including methods, apparatus, and compositions, for performing a multiplexed digital assay on a greater number of targets through combinatorial use of signals.

15 Claims, 10 Drawing Sheets

(56) References Cited

U.S. PATENT DOCUMENTS

| | | |
|---|---|---|
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 | 9/2008 | Hairston et al. |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Michael Corbett et al. |
| 2006/0014187 A1 | 1/2006 | Li et al. |
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |

(56) References Cited

U.S. PATENT DOCUMENTS

| | | |
|---|---|---|
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2007/0275415 A1 | 11/2007 | Srinivasan et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0233686 A1 | 9/2010 | Higuchi et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McClements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0194805 A1 | 8/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | WO 03/064691 A2 * | 8/2003 |
| WO | 03/072258 | 9/2003 |
| WO | 2004/040001 | 5/2004 |
| WO | 2005/007812 | 1/2005 |
| WO | 2005/010145 | 2/2005 |

(56) References Cited

FOREIGN PATENT DOCUMENTS

| WO | 2005/021151 | | 3/2005 |
|---|---|---|---|
| WO | 2005/023091 | | 3/2005 |
| WO | 2005/055807 | | 6/2005 |
| WO | 2005/073410 | | 8/2005 |
| WO | 2005/075683 | | 8/2005 |
| WO | WO 2006/002167 | A2 * | 1/2006 |
| WO | 2006/023719 | | 3/2006 |
| WO | 2006/027757 | | 3/2006 |
| WO | 2006/038035 | | 4/2006 |
| WO | 2006/086777 | | 8/2006 |
| WO | 2006/095981 | | 9/2006 |
| WO | 2007/091228 | | 8/2007 |
| WO | 2007/091230 | | 8/2007 |
| WO | 2007/092473 | | 8/2007 |
| WO | 2007/133710 | | 11/2007 |
| WO | 2008/021123 | | 2/2008 |
| WO | 2008/024114 | | 2/2008 |
| WO | 2008/063227 | | 5/2008 |
| WO | 2008/070074 | | 6/2008 |
| WO | 2008/070862 | | 6/2008 |
| WO | 2008/109176 | | 9/2008 |
| WO | 2008/109878 | | 9/2008 |
| WO | 2008/112177 | | 9/2008 |
| WO | 2009/002920 | | 12/2008 |
| WO | 2009/015863 | | 2/2009 |
| WO | 2009/049889 | | 4/2009 |
| WO | 2009/085246 | | 7/2009 |
| WO | 2010/001419 | | 1/2010 |
| WO | 2010/018465 | | 2/2010 |
| WO | 2010036352 | A1 | 4/2010 |
| WO | 2011/034621 | | 3/2011 |
| WO | 2011/079176 | | 6/2011 |

OTHER PUBLICATIONS

Young, Lee W., Authorized officer, International Searching Authority, International Search Report, PCT Patent Application Serial No. PCT/US2012/029712; search date: Aug. 7, 2012; mail date: Aug. 17, 2012.

Young, Lee W., Authorized officer, International Searching Authority, Written Opinion of the International Searching Authority, PCT Patent Application Serial No. PCT/US2012/029712; opinion date: Aug. 7, 2012; mail date: Aug. 17, 2012.

Zhong et al. Multiplex digital PCR: breaking the one target per color barrier of quantitative PCR. Lab Chip, 2011, 11, 2167-2174, published May 17, 2011.

J. Smid-Korbar et al., "Efficiency and usability of silicone surfactants in emulsions," International Journal of Cosmetic Science 12, pp. 135-139, (1990), presented at the 15$^{th}$ IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Shuming Nie et al., "Optical Detection of Single Molecules," Annu. Rev. Biophys. BiomoL Struct. vol. 26, pp. 567-596, (1997).

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al., "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

Shelley L. Anna et al., "Formation of dispersions using "flow focusing" in microchannels," Applied Physics Letters, vol. 82, No. 3, Jan. 20, 2003.

Goldschmidt GMBH, "Abil® EM 90 Emulsifier for the formulation of cosmetic W/O creams and lotions," degussa. creating essentials brochure, pp. 1-7, May 2003.

Purnendu K. Dasgupta et al., "Light emitting diode-based detectors Absorbance, fluorescence and spectroelectrochemical measurements in a planar flow-through cell," Analytica Chimica Acta 500, pp. 337-364, (2003).

(56) References Cited

OTHER PUBLICATIONS

R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Groff M. Schroeder et al., "Introduction to Flow Cytometry" version 5.1, 182 pgs. (2004).
Stéphane Swillens et al., "Instant evaluation of the absolute initial number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: a Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 19, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16th European Symposium on Computer Aided Process Engineering and 9th International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).

Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," Trends in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of -Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Dayong Jin et al., "Practical Time-Gated Luminescence Flow Cytometry. II: Experimental Evaluation Using UV LED Excitation," Cytometry Part A • 71A, pp. 797-808, Aug. 24, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.
Nicole Pamme, "continuous flow separations in microfluidic devices," Lab on a Chip, vol. 7, pp. 1644-1659, Nov. 2, 2007.

(56) References Cited

OTHER PUBLICATIONS

N. Reginald Beer et al., "On-Chip, Real-Time, Single-Copy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
SIGMA-ALDRICH, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Jian Qin et al., "Studying copy number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semisolid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Jiaqi Huang et al., "Rapid Screening of Complex DNA Samples by Single-Molecule Amplification and Sequencing," PLoS ONE, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 8-19, Aug. 2012.
Stavros Therianos et al., "Single-Channel Quantitative Multiplex Reverse Transcriptase-Polymerase Chain Reaction for Large Numbers of Gene Products Differentiates Nondemented from Neuropathological Alzheimer's Disease", American Journal of Pathology, vol. 164, No. 3, Mar. 2004, pp. 795-806.
Yolanda Schaerli et al., "The potential of microfluidic water-in-oil droplets in experimental biology", Molecular BioSystems, Royal Society of Chemistry, vol. 5, No. 12, Dec. 1, 2009, pp. 1392-1404.
Zhishan Hua et al., "Multiplexed Real-Time Polymerase Chain Reaction on a digital Microfluidic Platform", Analytical Chemistry, vol. 82, No. 6, Mar. 15, 2010, pp. 2310-2316.
European Patent Office, "Supplementary European Search Report" in connection with related European Patent Application No. 12760944.4, dated Jan. 15, 2015, 9 pages.

* cited by examiner

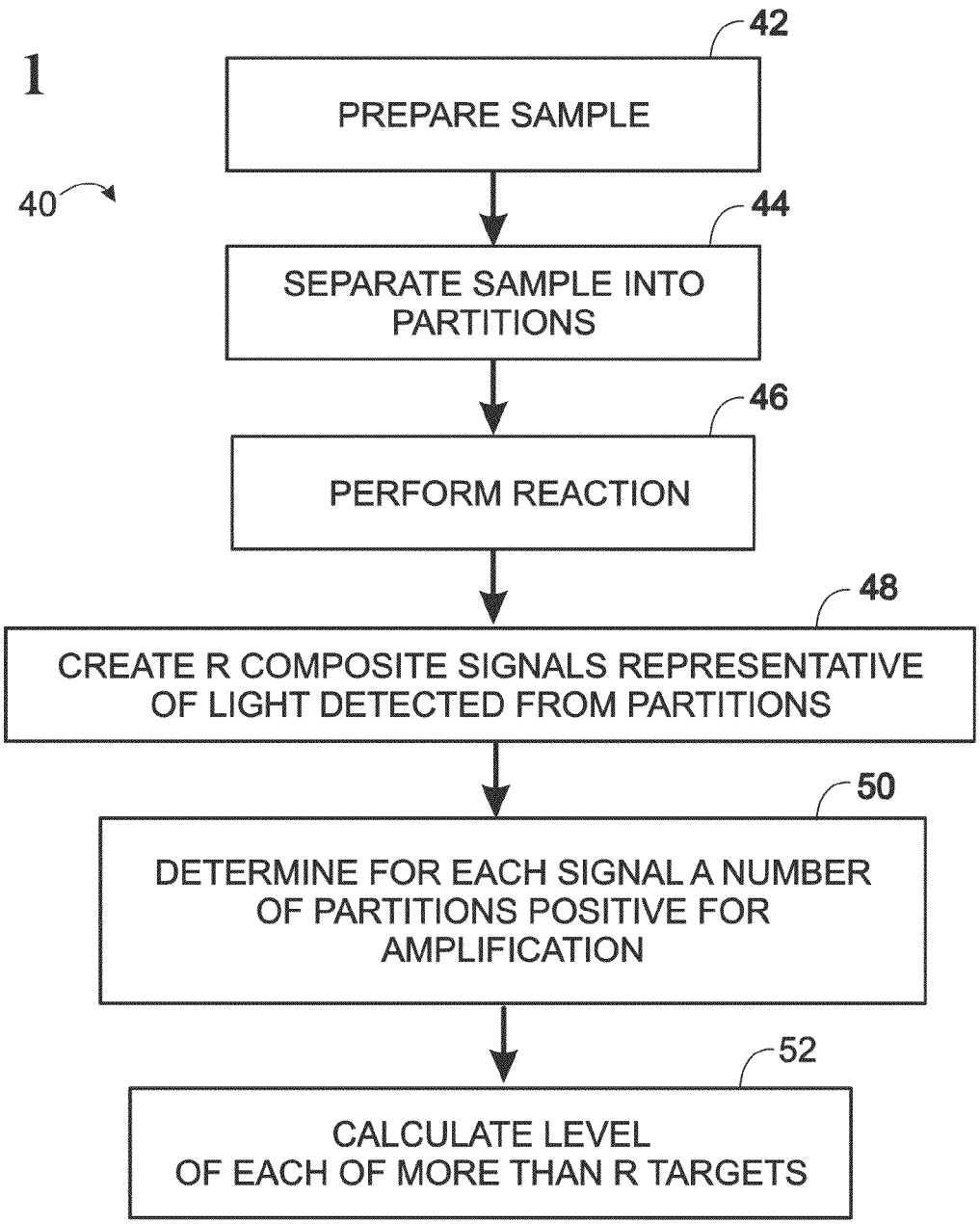
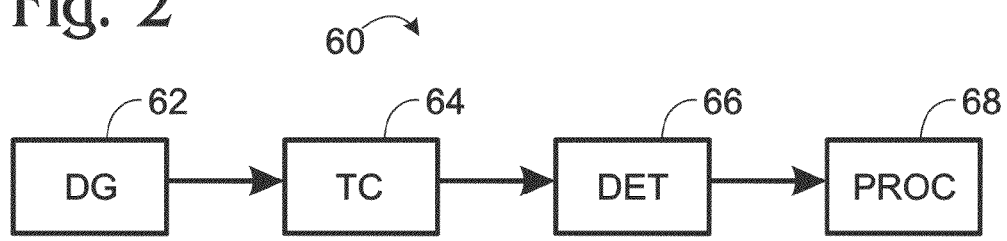

MULTIPLEXED DIGITAL ASSAYS WITH COMBINATORIAL USE OF SIGNALS

CROSS-REFERENCE TO PRIORITY APPLICATION

This application is based upon and claims the benefit under 35 U.S.C. §119(e) of U.S. Provisional Patent Application Ser. No. 61/454,373, filed Mar. 18, 2011, which is incorporated herein by reference in its entirety for all purposes.

CROSS-REFERENCES

This application incorporates by reference in their entireties for all purposes the following materials: U.S. Pat. No. 7,041,481, issued May 9, 2006; U.S. Patent Application Publication No. 2010/0173394 A1, published Jul. 8, 2010; PCT Patent Application Publication No. WO 2011/120006 A1, published Sep. 29, 2011; PCT Patent Application Publication No. WO 2011/120024 A1, published Sep. 29, 2011; U.S. patent application Ser. No. 13/287,120, filed Nov., 1, 2011; U.S. Provisional Patent Application Ser. No. 61/507,082, filed Jul. 12, 2011; U.S. Provisional Patent Application Ser. No. 61/510,013, filed Jul. 20, 2011; and Joseph R. Lakowicz, PRINCIPLES OF FLUORESCENCE SPECTROSCOPY ($2^{nd}$ Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the average concentration of analyte in the partitions may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized in a Poisson equation to determine the concentration of the analyte in the partitions.

Digital assays frequently rely on amplification of a nucleic acid target in partitions to enable detection of a single copy of an analyte. Amplification may be conducted via the polymerase chain reaction (PCR), to achieve a digital PCR assay. The target amplified may be the analyte itself or a surrogate for the analyte generated before or after formation of the partitions. Amplification of the target can be detected optically with a fluorescent probe included in the reaction. In particular, the probe can include a dye that provides a fluorescence signal indicating whether or not the target has been amplified.

A digital PCR assay can be multiplexed to permit detection of two or more different targets within each partition. Amplification of the targets can be distinguished by utilizing target-specific probes labeled with different dyes, which produce fluorescence detected in different detection channels, namely, at different wavelengths or wavelength regions ("colors") of emission (and/or excitation). If a detector for a digital PCR assay can distinguishably measure the fluorescence emitted by R different dyes, then the assay is effectively capable of measuring R different targets. However, instruments with more detection channels, to detect more colors, are more expensive than those with fewer detection channels. Also, increasing the number of distinguishable dyes is expensive and becomes impractical beyond a certain number. On the other hand, many applications, especially where sample is limited, could benefit greatly from higher degrees of multiplexing.

A new approach is needed to increase the multiplex levels of digital assays.

SUMMARY

The present disclosure provides a system, including methods, apparatus, and compositions, for performing a multiplexed digital assay on a greater number of targets through combinatorial use of signals.

BRIEF DESCRIPTION OF THE DRAWINGS

FIG. 1 is a flowchart of an exemplary method of performing a digital assay, in accordance with aspects of the present disclosure.

FIG. 2 is a schematic view of an exemplary system for performing the digital assay of FIG. 1, in accordance with aspects of the present disclosure.

DETAILED DESCRIPTION

Figure 3:
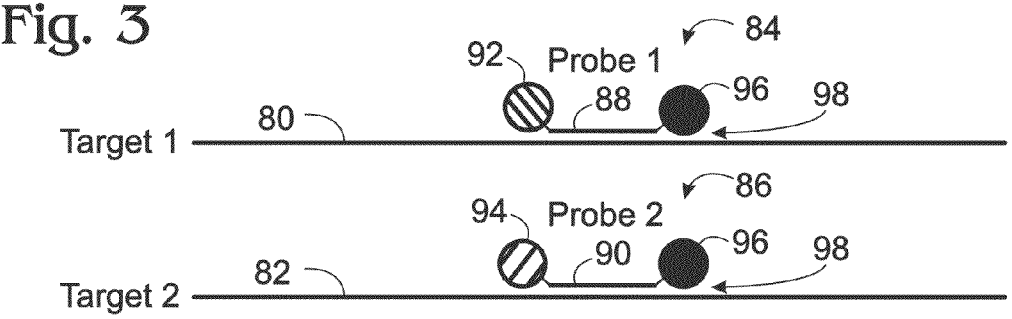
FIG. 3 is a schematic view of a pair of targets and corresponding probes capable of reporting the presence or absence of target amplification via emitted light that may be detected to create a dedicated signal for each target in a digital amplification assay, in accordance with aspects of the present disclosure.

The present disclosure provides a system, including methods, apparatus, and compositions, for performing a multiplexed digital assay on a greater number of targets through combinatorial use of signals. The method may be described as a color-based approach to multiplexing.

A method of performing a multiplexed digital amplification assay, such as a PCR assay, is provided. In the method, more than R targets may be amplified in partitions. R signals may be created. The signals may be representative of light detected in R different wavelength regimes from the partitions, where $R \geq 2$. An average level of each target in the partitions may be calculated based on the R signals, with the level calculated accounting for a coincidence, if any, of different targets in the same individual partitions.

Another method of performing a multiplexed digital amplification assay is provided. In the method, more than R targets may be amplified in droplets. R signals may be created, with the signals representative of light detected in R different wavelength regimes from the droplets, where $R \geq 2$. An average level of each of the more than R targets may be calculated by finding solutions to a set of simultaneous equations.

Yet another method of performing a multiplexed digital amplification assay is provided. In the method, R targets may be amplified in droplets. R signals may be created, where $R \geq 2$, with the signals representative of light detected in R different wavelength regimes from the droplets. Each of the signals may report amplification of a different combination of at least two of the targets. An average level of each target in the droplets may be calculated based on the R signals, without determining which of the at least two targets for each signal amplified in individual amplification-positive droplets for such signal.

A composition is provided. The composition may comprise a droplet containing a probe. The probe may include an oligonucleotide, a first fluorophore, a second fluorophore, and an energy transfer moiety. The energy transfer moiety may be a quencher and/or an energy transfer partner for one or both of the first and second fluorophores.

Further aspects of the present disclosure are presented in the following sections: (I) system overview, and (II) examples.

I. SYSTEM OVERVIEW

FIG. 1 shows a flowchart of an exemplary method 40 of performing a digital assay. The steps presented for method 40 may be performed in any suitable order and in any suitable combination. Furthermore, the steps may be combined with and/or modified by any other suitable steps, aspects, and/or features of the present disclosure.

A sample may be prepared for the assay, indicated at 42. Preparation of the sample may include any suitable manipulation of the sample, such as collection, dilution, concentration, purification, lyophilization, freezing, extraction, combination with one or more assay reagents, performance of at least one preliminary reaction to prepare the sample for one or more reactions in the assay, or any combination thereof, among others. Preparation of the sample may include rendering the sample competent for subsequent performance of one or more reactions, such as one or more enzyme catalyzed reactions and/or binding reactions.

In some embodiments, preparation of the sample may include combining the sample with reagents for amplification and for reporting whether or not amplification occurred. Such reagents may include any combination of primers for the targets (e.g., a forward primer and a reverse primer for each target), reporters (e.g., probes) for detecting amplification of the targets, dNTPs and/or NTPs, at least one enzyme (e.g., a polymerase, a ligase, a reverse transcriptase, or a combination thereof, each of which may or may not be heat-stable), or the like. Accordingly, preparation of the sample may render the sample (or partitions thereof) capable of amplification of each of one or more targets, if present, in the sample (or a partition thereof).

The sample may be separated into partitions, indicated at 44. Separation of the sample may involve distributing any suitable portion or all of the sample to the partitions. Each partition may be and/or include a fluid volume that is isolated from the fluid volumes of other partitions. The partitions may be isolated from one another by a carrier fluid, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with a droplet generator, by agitation of the sample (e.g., shaking, stirring, sonication, etc.), or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, or 1 µL, less than about 100, 10, or 1 nL, or less than about 100, 10, or 1 pL, among others.

The partitions, when formed, may be competent for performance of one or more reactions in the partitions. Alternatively, one or more reagents may be added to the partitions after they are formed to render them competent for reaction. The reagents may be added by any suitable mechanism, such as a fluid dispenser, fusion of droplets, or the like. Any of the reagents may be combined with the partitions (or a bulk phase sample) in a macrofluidic or microfluidic environment.

One or more reactions may be performed in the partitions, indicated at 46. Each reaction performed may occur selectively (and/or substantially) in only a subset of the partitions, such as less than about one-half, one-fourth, or one-tenth of the partitions, among others. The reaction may involve a target, which may, for example, be a template and/or a reactant (e.g., a substrate), and/or a binding partner, in the reaction. The reaction may occur selectively (or selectively may not occur) in partitions containing at least one copy of the target.

The reaction may or may not be an enzyme-catalyzed reaction. In some examples, the reaction may be an amplification reaction, such as a polymerase chain reaction and/or ligase chain reaction. Accordingly, a plurality of amplification reactions for a plurality of targets may be performed simultaneously in the partitions.

Performing a reaction may include subjecting the partitions to one or more conditions that promote occurrence of the reaction. The conditions may include heating the partitions and/or incubating the partitions at a temperature above room temperature. In some examples, the conditions may include thermally cycling the partitions to promote a polymerase chain reaction and/or ligase chain reaction.

R signals may be created that are representative of light detected from the partitions, indicated at 48. The R signals may be 2, 3, 4, or more signals. In some examples, light corresponding to each signal may be detected with a distinct sensor, and/or light corresponding to at least two signals may be detected at different times with the same sensor. The R signals may correspond to light detected in respective wavelength regimes that are different from one another. Each wavelength regime may be characterized by a wavelength(s) or and/or wavelength range(s) at which the partitions are illuminated (e.g., with excitation light) and/or a wavelength(s) or and/or wavelength range(s) at which light from the partitions is detected (e.g., emitted light). The light detected may be light emitted from one or more fluorophores.

Each of the R signals may be created in a distinct detection channel. Accordingly, R signals may be created in R detection channels.

Each signal may be a composite signal that represents two, three, four, or more reactions/assays and thus two, three, four, or more targets of the reactions/assays. The composite signal may include two or more integral signal portions that each represent a different reaction/assay and target. Analysis of one of the composite signals by itself, without the benefit of data from the other composite signals, may (or may not) permit estimation of a collective concentration, but not individual concentrations, for two or more targets represented by the composite signal. Instead, as described further below, analysis of the composite signals together permits calculation of the concentration of each target. (The terms "estimation" and "calculation" are used interchangeably.)

The R composite signals (and/or R detection channels) may represent more than R reactions and/or targets, with the number of reactions/assays and targets depending on configuration. For example, the R signals may be or include two composite signals (arbitrarily termed α and β) collectively representing three reactions/assays and/or three targets (arbitrarily termed 1, 2, and 3), with each composite signal representing a different combination of two reactions/assays/targets (e.g., targets 1 and 2 for α and targets 1 and 3 for β). Alternatively, the R signals may be three composite signals (arbitrarily termed α, β, and γ) collectively representing up to seven reactions/assays/targets (1 to 7), if each composite signal represents a different combination of up to four reactions/assays/targets each (e.g., targets 1, 2, 3, and 4 for α; targets 2, 4, 5, and 6 for β; and targets 3, 4, 6, and 7 for γ). The R signals may be four composite signals representing up to fifteen reactions/assays/targets, if each composite signal represents a different combination of up to eight reactions/assays/targets each.

More generally, $2^R-1$ targets can be assayed with R composite signals (or wavelength regimes). To assay $2^R-1$ targets in R wavelength regimes, each target may be represented by a different wavelength regime or combination of wavelength regimes than every other target. A set of $2^R-1$ targets can be represented and assayed when all of the wavelength regimes have been utilized individually and in all possible combinations.

Each composite signal may be created based on detected light emitted from one or more probes in the partitions. The one or more probes may report whether at least one of two or more particular reactions represented by the signal has occurred in a partition and thus whether at least one copy of at least one of two or more particular targets corresponding to the two or more particular reactions is present in the partition. The intensity of a composite signal corresponding to the probes may be analyzed to determine whether or not at least one of the particular reactions has occurred and at least one copy of one of the particular targets is present. The intensity may vary among the partitions according to whether at least one of the particular reactions occurred or did not occur (e.g., above a threshold extent) and at least one of the particular targets is present in or absent from each individual partition.

The probes represented by a composite signal may include different fluorophores. In other words, light emitted from different fluorophores may be detected to create at two different integral portions of the composite signal for a particular wavelength regime. Alternatively, or in addition, the same fluorophore may be included in one probe or two or more probes for at least two targets represented by the composite signal. In some cases, the same fluorophore may be included in a probe for each target represented by the composite signal.

Each probe may include a nucleic acid (e.g., an oligonucleotide) and at least one fluorophore. Different probes with different oligonucleotide sequences and/or different fluorophores (or fluorophore combinations) may be used to create at least two different integral portions of the signal. Alternatively, or in addition, the same probe may be used as a reporter for at least two different targets represented by the composite signal (e.g., see Examples 3-5). In some cases, the same probe may be used as a reporter for each target represented by the composite signal.

The composite signal detected from each partition, and the partition itself, may be classified as being positive or negative for the reactions/assays/targets represented by the signal or corresponding wavelength regime. Classification may be based on the strength of the signal. If the signal/partition is classified as positive, at least one of the reactions/assays represented by the signal is deemed to have occurred and at least one copy of at least one of the targets represented by the signal is deemed to be present in the partition. In contrast, if the signal/partition is classified as negative, none of the reactions/assays represented by the signal is deemed to have occurred and no copy of any of the targets represented by the signal is deemed to be present in the partition.

The composite signals collectively permit estimation of target concentrations by representation of a different combination of targets in each detection channel. Accordingly, each target, when present without any of the other targets in a partition, may produce a unique target signature among the wavelength regimes. For example, some of the targets, if present alone in a partition, may selectively change the signal strength for only one wavelength regime. Others of the targets, if present alone in a partition, may selectively change the signal strength for a unique combination of two of the wavelength regimes, still other targets may selectively change the signal strength for a unique combination of three of the wavelength regimes, and so on, optionally up to the number of wavelength regimes/detection channels.

A fraction of the partitions may have a coincidence of different targets, where each of these partitions contains a copy of each of two or more targets in the same individual partitions. Moreover, each of these partitions may contain a copy of each of two or more distinct targets, which, for a particular partition, collectively may produce a signature that is the same as that of a target not present in the partition. However, the fraction of partitions containing two or more distinct targets may (or may not) be kept relatively low, by working in a dilute regime, such as with less than about one-half, one-fifth, or one-tenth, among others, of the partitions containing more than one target molecule when the partitions are formed. In any event, a suitable estimation of concentration, as described below, may take into account the occurrence of two or more target molecules, representing the same target or different targets, in the same individual partitions. Alternatively, if working in a sufficiently dilute regime, the occurrence of two or more target molecules per partition may be sufficiently rare to ignore for a desired accuracy of concentration.

A number of partitions that are positive may be determined for each signal, indicated at 50. For example, a number of partitions that are positive only for each particular composite signal or corresponding wavelength regime/detection channel may be determined individually (e.g., counted) for each signal or channel (i.e., a number for each channel). Also, a number of partitions that are positive only for each particular combination (or at least one combination or each of two or more combinations) of composite signals or corresponding wavelength regimes may be determined individually (e.g., counted) for each combination of signals or channels (i.e., a number for each combination, and particularly each combination corresponding to a particular target).

A distinct fraction of the partitions positive for each signal alone and for each signal combination may be determined. The fraction for each signal or signal combination may be determined by dividing the number of partitions for the signal/combination, determined at 50, by the total number of partitions from which signals are detected. The total number of partitions may be counted or estimated.

A level of each target may be calculated, indicated at 52. The level may be an average level, such as an average concentration of molecules of the target per partition. Generally, if R signals are detected from the partitions in R wavelength regimes, the average level of each of more than R targets (e.g., up to $2^R-1$ targets) may be calculated. The level of each target may be calculated based on the respective numbers of partitions positive for each signal alone and signal combination. The calculation may be based on copies of each target having a Poisson distribution among the partitions. The concentrations may, for example, be calculated by finding solutions to a series of simultaneous equations (interchangeably termed a set of simultaneous equations), each having the same variables. The simultaneous equations may be linear equations. Alternatively, or in addition, each equation may contain at least $2^R-1$ variables. The solutions may be found by numerical analysis, also termed numerical approximation. Further aspects of calculating average target levels are described elsewhere in the present disclosure, such as in Examples 6 and 7.

FIG. 2 shows an exemplary system 60 for performing the digital assay of FIG. 1. System 60 may include a partitioning assembly, such as a droplet generator 62 ("DG"), a thermal incubation assembly, such as a thermocycler 64 ("TC"), a detection assembly (a detector) 66 ("DET"), and a data processing assembly (a processor) 68 ("PROC"), or any combination thereof, among others. The data processing assembly may be, or may be included in, a controller that communicates with and controls operation of any suitable combination of the assemblies. The arrows between the assemblies indicate optional movement or transfer, such as movement or transfer of fluid (e.g., a continuous phase of an emulsion) and/or partitions (e.g., droplets) or signals/data. Any suitable combination of the assemblies may be operatively connected to one another, and/or one or more of the assemblies may be unconnected to the other assemblies, such that, for example, material/data is transferred manually.

System 60 may operate as follows. Droplet generator 62 may form droplets disposed in a carrier fluid, such as a continuous phase. The droplets may be cycled thermally with thermocycler 64 to promote amplification of targets in the droplets. Composite signals may be detected from the droplets with detector 66. The signals may be processed by processor 68 to calculate levels of the targets.

Further aspects of sample preparation, droplet generation, assays, reagents, reactions, thermal cycling, detection, and data processing, among others, that may be suitable for the methods and systems disclosed herein, are described below and in the documents listed above under Cross-References, which are incorporated herein by reference, particularly U.S. Patent Application Publication No. 2010/0173394 A1, published Jul. 8, 2010; PCT Patent Application Publication No. WO 2011/120006 A1, published Sep. 29, 2011; PCT Patent Application Publication No. WO 2011/120024 A1, published Sep. 29, 2011; and U.S. patent application Ser. No. 13/287,120, filed Nov., 1, 2011.

II. EXAMPLES

This section presents selected aspects and embodiments of the present disclosure related to methods and compositions for performing multiplexed digital assays. These aspects and embodiments are included for illustration and are not intended to limit or define the entire scope of the present disclosure.

Example 1

Digital Amplification Assays with Dedicated Signals and Composite Signals

Figure 4:
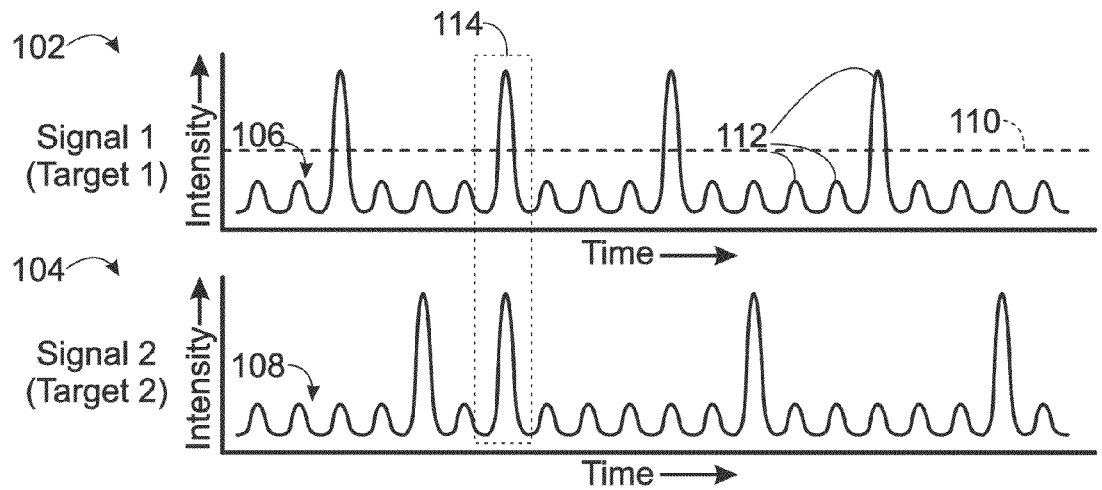
FIG. 4 is a pair of exemplary graphs of respective dedicated signals that may be created by detecting light emitted from the probes of FIG. 3 in a digital amplification assay performed in droplets, with each signal created from light detected over the same time interval from a fluid stream containing the droplets, in accordance with aspects of the present disclosure.
Figure 5:
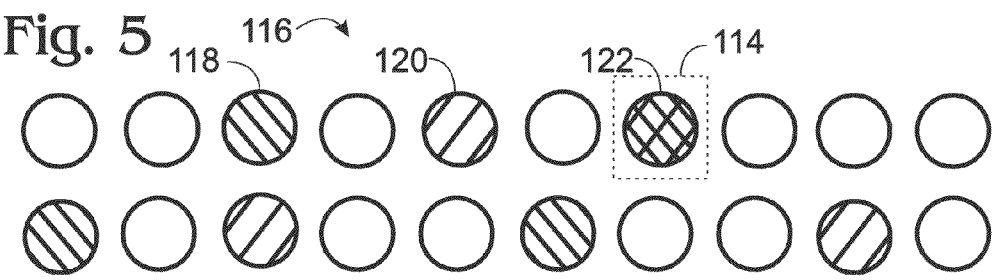
FIG. 5 is a schematic representation of how copies of the pair of targets of FIG. 3 are distributed among the droplets from which light is detected in FIG. 4, based on the intensity of the respective dedicated signals of FIG. 4, in accordance with aspects of the present disclosure.
Figure 6:
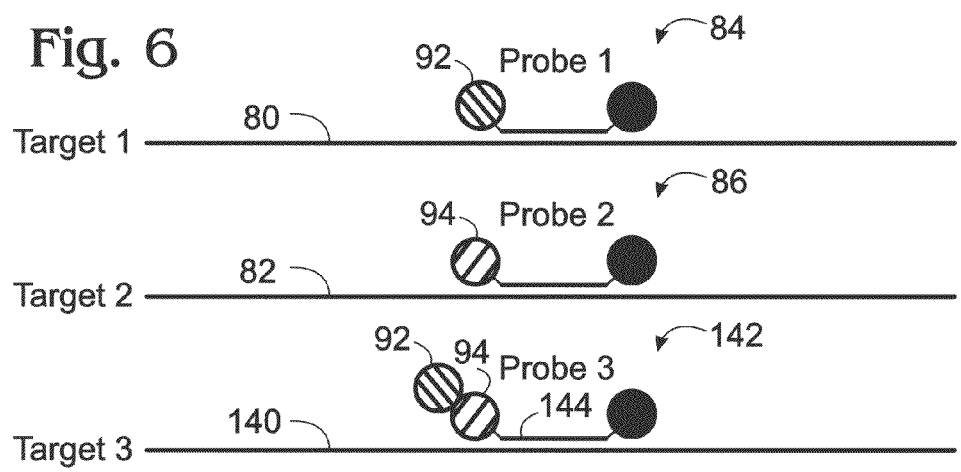
FIG. 6 is a schematic view of three targets and corresponding exemplary probes capable of reporting the presence or absence of target amplification via emitted light that may be detected to create a pair of composite signals in a digital amplification assay, in accordance with aspects of the present disclosure.
Figure 7:
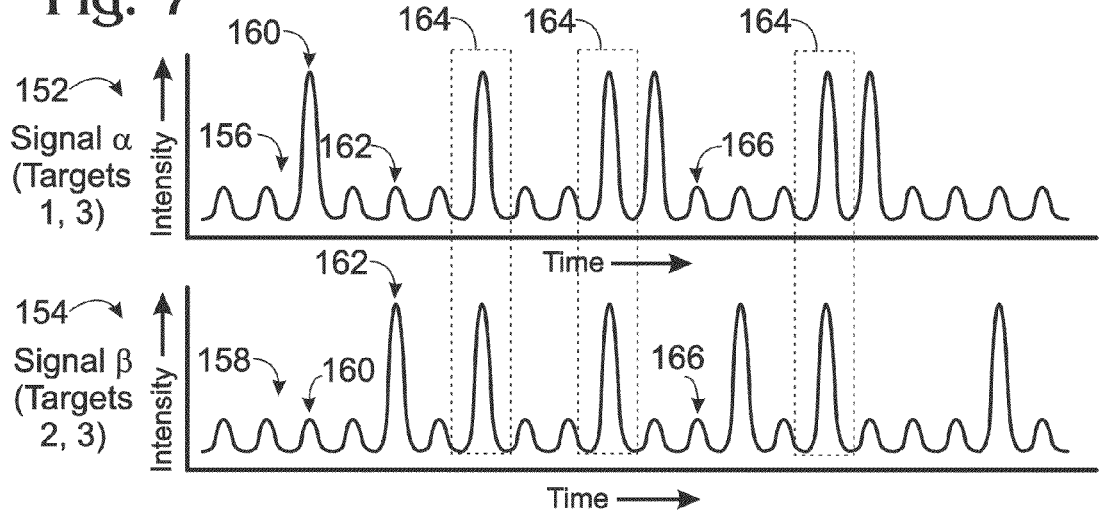
FIG. 7 is a pair of exemplary graphs of a pair of composite signals that may be created by detecting fluorescence emission from the three probes of FIG. 6 in a digital amplification assay performed in droplets, with emitted light detected in two different wavelength regimes over the same time interval from a fluid stream containing the droplets, in accordance with aspects of the present disclosure.
Figure 8:
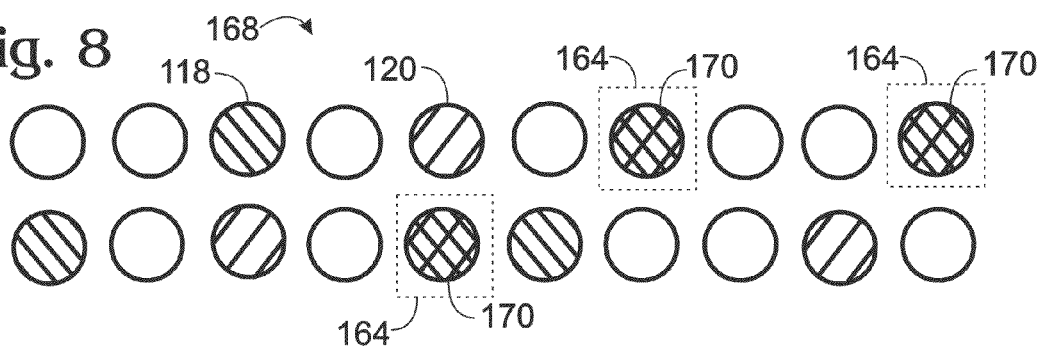
FIG. 8 is a schematic representation of how copies of the three targets of FIG. 6 are distributed among the droplets from which light is detected in FIG. 7, based on the intensity of the respective composite signals of FIG. 7, in accordance with aspects of the present disclosure.

This example compares and contrasts exemplary digital amplification assays utilizing (i) a pair of dedicated signals for two targets, see FIGS. 3-5, and (ii) a pair of composite signals for three targets, see FIGS. 6-8. The principles explained here may be extended to R signals for $2^R-1$ targets.

FIG. 3 shows a pair of nucleic acid targets 80, 82 ("Target 1" and "Target 2") and corresponding probes 84, 86 ("Probe 1" and "Probe 2") that may be used to create a dedicated signal for amplification of each target in a digital amplification assay. Each probe may include an oligonucleotide 88, 90, a fluorophore 92, 94, and a quencher 96. The fluorophore(s) and quencher are associated with and/or attached to the oligonucleotide, such as attached covalently. The probe also or alternatively may include a binding moiety (a minor groove binder) for the minor groove of a DNA duplex, which may be conjugated to the oligonucleotide and may function to permit a shorter oligonucleotide to be used in the probe. The probe may be a TaqMan probe, a molecular beacon probe, a scorpion probe, a locked nucleic acid probe, or the like.

Each oligonucleotide may provide target specificity by hybridization predominantly or at least substantially exclusively to an amplicon produced by amplification of only one of the two targets. Hybridization of the oligonucleotide to its corresponding target/amplicon is illustrated schematically at 98.

Fluorophores 92, 94 may be optically distinguishable from each other, as illustrated schematically by a distinct hatch pattern for each fluorophore. For example, the fluorophores may have distinct absorption spectra and/or maxima, and/or distinct emission spectra and/or emission maxima. Proper selection of the wavelength regime used for detection allows the fluorophores to be distinguished. In other words, the wavelength or wavelength band of excitation light used for each wavelength regime and/or the wavelength or wavelength band of emitted light received and sensed by the sensor for the wavelength regime provides selective detection of light from only one of the fluorophores in the detection channel. Exemplary fluorophores that may be suitable include FAM, VIC, HEX, ROX, TAMRA, JOE, etc.

Quencher 96 is configured to quench the signal produced by fluorophore 92 or 94 in a proximity-dependent fashion. Light detected from the fluorophore may increase when the associated oligonucleotide 88 or 90 binds to the amplified target, to increase the separation distance between the fluorophore and the quencher, or when the probe is cleaved during target amplification, among others. In some cases, the quencher may be replaced by, or supplemented with, a fluorophore that is capable of energy transfer with fluorophore 92 or 94.

FIG. 4 shows a pair of exemplary graphs 102, 104 of data collected in an exemplary digital amplification assay for Target 1 and Target 2 performed in droplets. Each graph plots a dedicated signal 106 ("Signal 1") or signal 108 ("Signal 2") that represents light detected from respective probes 84, 86 (and/or one or more modified (e.g., cleavage) products thereof) (see FIG. 3). Each dedicated signal is created from light detected over the same time period from a fluid stream containing the droplets and flowing through an examination region of a channel. Signal 1 reports whether or not Target 1 is present in each droplet, and Signal 2 reports whether or not Target 2 is present in each target. In particular, if the strength of Signal 1 (or Signal 2) increases above a threshold 110, then Target 1 (or Target 2) is deemed to be present (and amplified) in a corresponding droplet. In the present illustration, each droplet, whether positive or negative for each target, produces an increase in signal strength above the baseline signal that forms an identifiable peak 112. Accordingly, each signal may vary in strength with the presence or absence of a droplet and with the presence or absence of a corresponding target.

Each target is present here at an average level (or frequency) of about 0.2 in the droplets. In other words, each target is amplified and detected on average about once every five droplets. Accordingly, the expected frequency of droplets containing both targets is the product of the two droplet frequencies, or about 0.04 (1 out of every 25 droplets). Consistent with this frequency, a droplet that is positive for both targets is present only once on the twenty droplets analyzed here, and is indicated by a dashed box at 114 extending around the signal peaks for the droplet in graphs 102, 104.

FIG. 5 schematically represents the distribution of Targets 1 and 2 in a set of droplets 116 corresponding to and in the same order as the droplet signal peaks of FIG. 4. Droplets positive for Signal 1, such as the droplet indicated at 118, are hatched according to fluorophore 92, and droplets positive for Signal 2, such as the droplet indicated at 120, are hatched according to fluorophore 94 (see FIG. 3). A double-positive droplet 122 containing both Target 1 and Target 2 is double-hatched and indicated by dashed box 114.

FIG. 6 shows three targets 80, 82, and 140 and corresponding exemplary probes 84, 86, and 142, respectively, that may be used to create a pair of composite signals for the three targets in a digital amplification assay. Two of the targets and probes, namely, targets 80 and 82 (Target 1 and Target 2) and probes 84 and 86 (Probe 1 and Probe 2) are the same targets and probes shown and utilized in FIGS. 3-5. Target 140 (Target 3) and its corresponding probe 142 (Probe 3) may be introduced into the multiplexed assay of FIGS. 3-5 to increase the level of multiplexing and the amount of target information that can be extracted from the assay without increasing the number of detection channels.

Amplification of Target 3 is reported by Probe 3. The probe includes an oligonucleotide 144 that hybridizes specifically to Target 3 (and/or an amplicon thereof), relative to Targets 1 and 2. The probe may be double-labeled with the same fluorophores (92, 94) present individually in Probe 1 and Probe 2 for reporting respective Target 1 and Target 2 amplification. The probes for the three targets may be selected to permit detection of target amplification in only two detection channels, rather than the three detection channels that would be necessary with the use of a dedicated detection channel for each target. Examples 2-5 describe other exemplary probe configurations that may be suitable to increase the level of multiplexing.

FIG. 7 shows a pair of exemplary graphs 152, 154 of a pair of composite signals 156, 158 that may be detected in a pair of wavelength regimes/detection channels. The composite signals, arbitrarily designated α and β, are representative of light detected from the three probes of FIG. 6 in a digital amplification assay performed in droplets. Each composite signal is created from light detected over the same time period from a fluid stream containing the droplets. To simplify the presentation, Target 1 and Target 2 are present at the same frequency and in the same droplets as in FIGS. 4 and 5.

Each composite signal, α or β (156 or 158), represents a pair of targets. Signal a (graph 152) has a strength for each droplet that indicates whether the droplet is positive or negative for at least one member of a first pair of targets, namely, Target 1 and Target 3. Signal β (graph 154) has a strength for each droplet that indicates whether the droplet is positive or negative for at least one member of a different second pair of targets, namely, Target 2 and Target 3. Accordingly, each composite signal analyzed by itself may provide no information about how frequently a given member of the pair of targets is present in droplets.

The composite signals analyzed in combination provide additional information about target frequency that cannot be deduced from the composite signals in isolation from one another. Each target, when present without other targets in a droplet, produces a signal signature that is distinct from the signatures of each other target individually. The signature for Target 1 in a droplet is indicated at 160: positive for Signal α and negative for Signal β. The signature for Target 2 in a droplet is indicated at 162: negative for Signal α and positive for Signal β. Furthermore, the signature for Target 3 in a droplet is outlined by dashed boxes at 164: positive for both Signal α and Signal β. Finally, the signature for none of Targets 1, 2, and 3 in a droplet is indicated at 166: negative for both Signal α and Signal β.

FIG. 8 schematically represents the distribution of Targets 1, 2, and 3 in a set of droplets 168 corresponding to and in the same order as the droplet signal peaks of FIG. 7. Single-positive droplets that are positive for Signal α only, such as the droplet indicated at 118, are hatched according to fluorophore 92, and droplets positive for Signal β, such as the droplet indicated at 120, are hatched according to fluorophore 94 (see FIG. 6). Each double-positive droplet 170 is double-hatched and indicated by dashed box 164.

The single-positive signatures indicated at 160 and 162 unambiguously identify corresponding droplets 118, 120 as containing at least one copy of Target 1 or Target 2, respectively, and no copy of Target 3. Accordingly, the number of each type of single-positive droplet may be used, in a ratio with the total number of droplets, to calculate an average level of Target 1 and of Target 2. However, this estimate may not be accurate enough if droplets contain multiple target molecules, because the estimate ignores any droplets containing Target 1 and/or Target 2, but having the signature of Target 3. These droplets can produce the same Target 3 signature while containing Targets 1+2, Targets 1+3, or Targets 2+3. If the concentration of each target is low enough, the frequency of droplets containing at least two different targets may be negligible and/or ignored. Here, the concentrations of Targets 1, 2, and 3 are high enough to produce, on average, only about one droplet with both of Targets 1 and 2 per twenty droplets (see FIGS. 4 and 5). Accordingly, one of double-positive droplets 170 is expected to contain both of Targets 1 and 2, and the other two double-positive droplets are expected to contain Target 3.

It is not necessary to know the target composition of each double-positive droplet. Instead, it is sufficient to know the frequency of droplets with each target signature. Poisson statistics then may be utilized to calculate the average level of each target. Calculation may be performed, in some cases by finding solutions to a series of simultaneous equations, such as numerically, to obtain a best-fit, or by a closed-form approach, among others.

Example 2

Exemplary Target-Specific Probes for Composite Signals

Figure 9A:
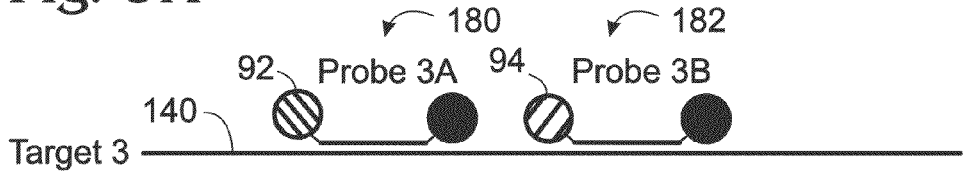
FIG. 9A is a schematic view of the third target of FIG. 6 and another exemplary probe configuration capable of reporting the presence or absence of third target amplification via emitted light, which may be used in conjunction with the first and second target probes of FIG. 6 to create only a pair of composite signals representing amplification of the three targets in a digital amplification assay, in accordance with aspects of the present disclosure.
Figure 9B:
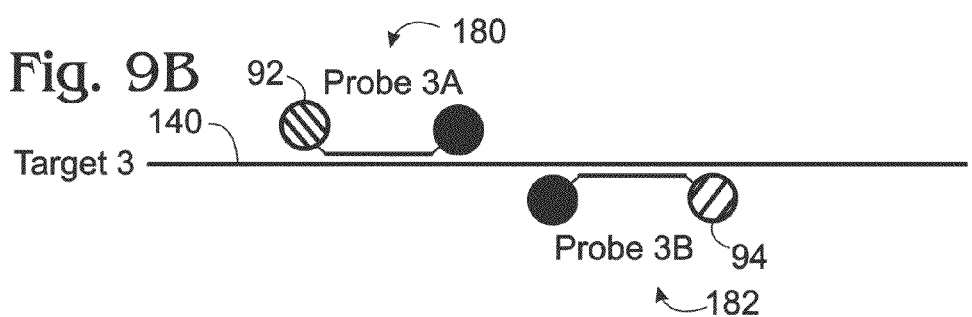
FIG. 9B is a schematic view of the third target of FIG. 6 and yet another exemplary probe configuration specific for the third target, which may be used in conjunction with the first and second target probes of FIG. 6 to create only a pair of composite signals representing the three targets in a digital amplification assay, in accordance with aspects of the present disclosure.
Figure 10:
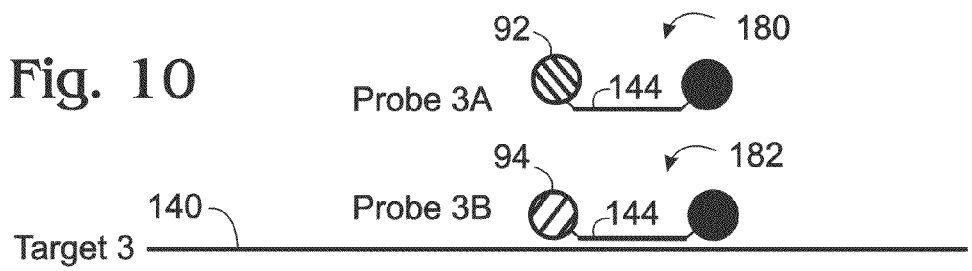
FIG. 10 is a schematic view of the third target of FIG. 6 and still another exemplary probe configuration capable of reporting the presence or absence of third target amplification via emitted light, which may be used in conjunction with the first and second target probes of FIG. 6 to create only a pair of composite signals representing amplification of the three targets in a digital amplification assay, in accordance with aspects of the present disclosure.

This example describes additional, exemplary target-specific probes that may be utilized in any suitable multiplexed digital assay; see FIGS. 9A, 9B, and 10. The principles explained here may be extended to any number of signals and/or targets.

FIGS. 9A, 9B, and 10 shows third target 140 of FIG. 6 and other exemplary probe configurations of probes 180, 182 (Probes 3A and 3B) each specific for Target 3 (and/or an amplicon thereof). Probes 3A and 3B may be used together, in place of Probe 3 of FIG. 6, and in conjunction with Probe 1 and Probe 2 of FIG. 6, to create only a pair of composite signals for Targets 1 to 3 in a digital amplification assay.

One of the probes (e.g., Probe 3A) may include fluorophore 92 and the other probe (e.g., Probe 3B) may include fluorophore 94. Accordingly, light emitted by Probe 3A can be detected in the same detection channel as light from Probe 1 of FIG. 6, and light emitted by Probe 3B in the same channel as Probe 2.

FIGS. 9A and 9B show Probes 3A and 3B binding specifically to distinct sites of Target 3. The probes may bind to non-overlapping (or only partially overlapping) sites on the same strand of the target (FIG. 9A). Alternatively, the probes may bind to opposite strands of Target 3 (FIG. 9B).

FIG. 10 shows Probes 3A and 3B that are capable of binding to the same site of Target 3 (and/or an amplicon thereof). Each of the probes may contain the same oligonucleotide 144 and thus differ only by the particular fluorophore (92 or 94) attached to oligonucleotide 144. The probes of this example may be blended in any suitable ratio or set of different ratios for a multiplexed assay.

Example 3

Exemplary Tailed Primers and Shared Probes for Composite Signals

Figure 11:
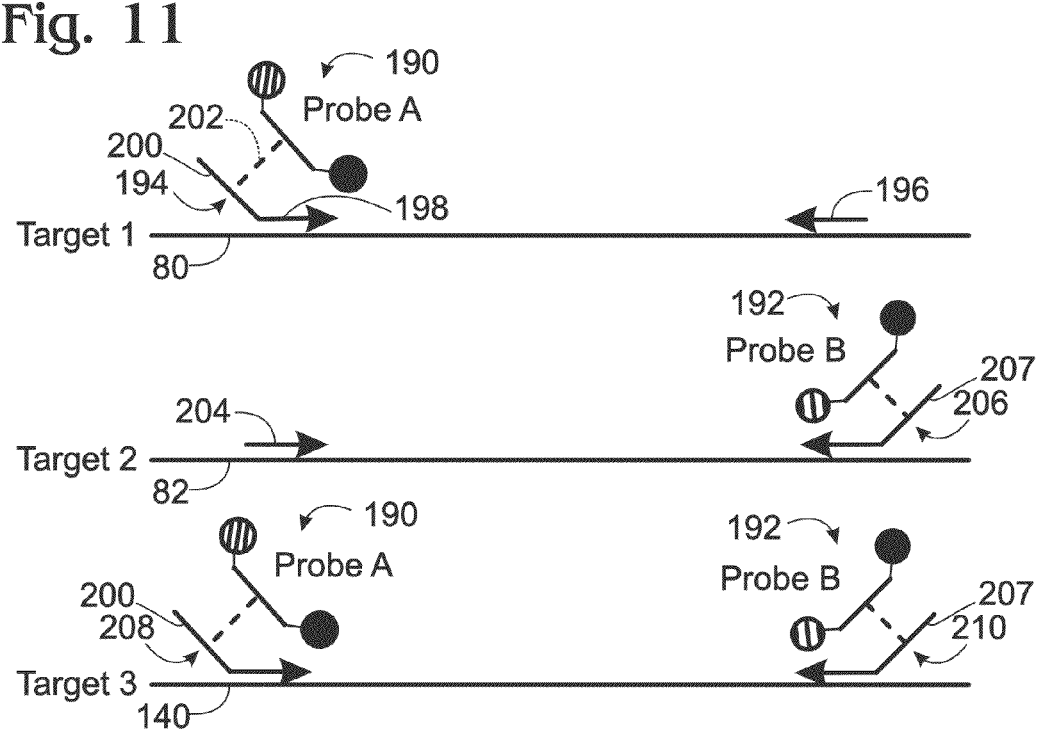
FIG. 11 is a schematic view of three targets and corresponding exemplary primers that enable use of only two probes to report amplification of the three targets in a digital amplification assay, in accordance with aspects of the present disclosure.

This example describes exemplary shared probes that enable creation of composite signals, and exemplary tailed primers forming binding sites for the shared probes; see FIG. 11. The principles explained here may be extended to any suitable number of composite signals and/or targets.

FIG. 11 shows three targets 80, 82, and 140 (i.e., Targets 1 to 3 of FIG. 6) and corresponding primers that enable assay of the three targets with only two probes, namely, probe 190 (Probe A) and probe 192 (Probe B), in a digital amplification assay. Probe A and Probe B may include respective fluorophores and a quencher (e.g., see FIG. 3).

Target 1 may be amplified with a pair of forward and reverse primers 194, 196. Forward primer 194 may be a tailed primer with a 3' binding portion 198 that is complementary to a region of Target 1 and a 5' tail portion 200 that is not. The tail portion may introduce a binding site for Probe A into the resulting amplicon, indicated by a dashed line at 202, such that Probe A (like Probe 1 of FIG. 6) can report amplification of Target 1.

Target 2 may be amplified with a pair of forward and reverse primers 204, 206. Reverse primer 206 may be structured analogously to forward primer 194 for Target 1, with a 3' binding portion complementary to a region of Target 2 and a 5' tail portion 207 that is not. The tail portion may introduce a binding site for Probe B into the resulting amplicon, such that Probe B (like Probe 2 of FIG. 6) can report amplification of Target 2.

Target 3 may be amplified with a pair of forward and reverse primers 208, 210. Both of the primers may be structured analogously to forward primer 194, with a 3' binding portion complementary to a region of Target 3 and a 5' tail portion that is not. Tail portions 200, 207 of primers 208, 210 may introduce respective binding sites for Probes A and B into the amplified product, such that a combination of both Probe A and Probe B (like Probe 3 of FIG. 6) reports amplification of Target 3.

Example 4

Exemplary Ligation Strategy to Enable Shared Probes

Figure 12:
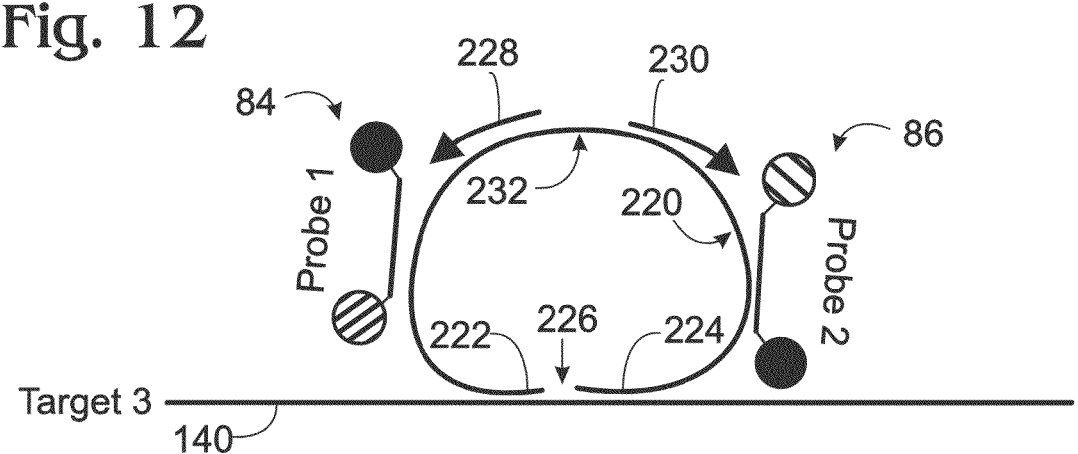
FIG. 12 is a schematic view of the third target of FIG. 6 and another exemplary probe and primer configuration that enables use of only two probes to report amplification of three targets in a digital amplification assay, in accordance with aspects of the present disclosure.

This example describes an exemplary ligation strategy to enable the use of shared probes; see FIG. 12. The principles explained here may be extended to any number of composite signals and/or targets.

FIG. 12 shows Target 3 (at 140) of FIG. 6 and another exemplary probe and primer configuration that enables assay of Targets 1 to 3 of FIG. 6 in a digital amplification assay with only Probes 1 and 2 (at 84 and 86) of FIG. 6. The ligation, extension, and digestion steps presented below may be performed in any suitable order and before or after a sample providing Target 3 is separated into partitions.

A template 220 (and/or a complementary strand and/or amplicon thereof) may be designed to bind each of Probes 1 and 2.

Template 220 also may be designed to bind to adjacent regions of Target 3 via opposing end regions 222, 224 of the template. (The template may be described as a molecular inversion "probe," but is generally not attached to a fluorophore.) The 5' and 3' termini of the template may be joinable directly to one another by ligation when bound to Target 3 or may form a gap 226 of one or more nucleotides between the aligned 5' and 3' termini of the template. The gap may be closed by extending the 3' terminus of the template, while bound to Target 3, before ligation of the template to form a closed loop. After ligation, and optional extension, copies of the template that fail to ligate (and thus have not found a copy of Target 3 for binding), may be degraded by an exonuclease. Ligated copies of the template may be resistant to this degradation, such that the number of ligated template molecules corresponds to the number of Target 3 molecules.

Ligated template 220 (and/or a complementary strand thereof) may provide one or more sites for binding of at least one primer 228 (or 230). The primer may amplify the ligated template by rolling circle amplification. Alternatively, or in addition, a pair of primers 228, 230 (forward and reverse) may be included to produce a cascade of amplification. In some embodiments, ligated template 220 may be linearized by cleavage at a predefined site 232 before amplification with primers 228, 230. In any event, the presence of Target 3 in partitions is reported by a combination of both Probes 1 and 2 in this embodiment.

Example 5

Exemplary Shared Probes with Multi-target Specificity

Figure 13:
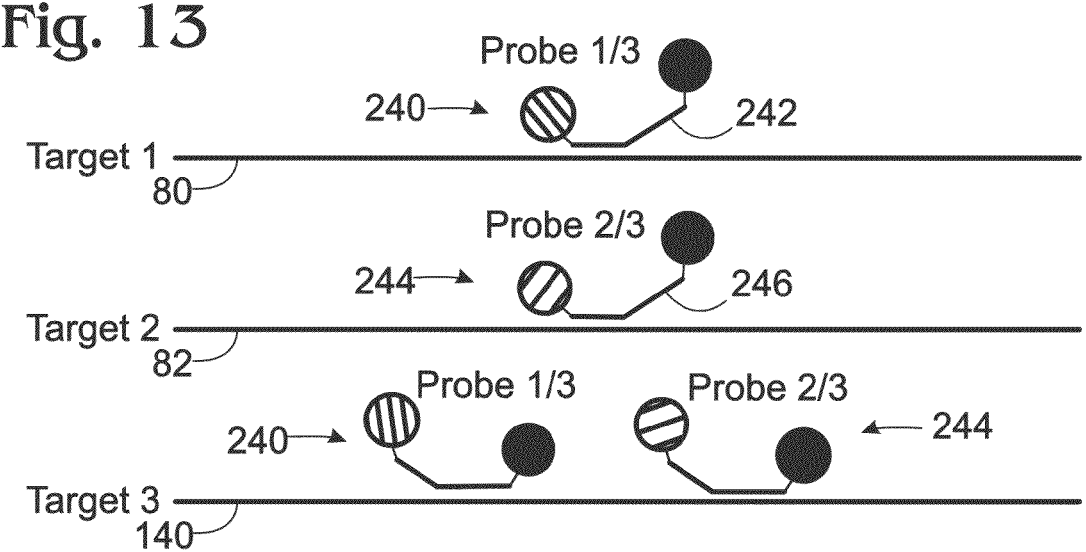
FIG. 13 is a schematic view of the three targets of FIG. 6 with yet another exemplary configuration of only two probes that enables use of the two probes to report amplification of three targets in a digital amplification assay, in accordance with aspects of the present disclosure.

This example describes exemplary shared probes each capable of binding to sequence regions of two different targets; see FIG. 13. The principles explained here may be extended to any number of composite signals and/or targets.

FIG. 13 shows targets 80, 82, 140 (i.e., Targets 1 to 3) bound by probes with multi-target specificity. In particular, a probe 240 (Probe 1/3) includes an oligonucleotide 242 capable of binding to a sequence region present in Target 1 and another sequence region present in Target 3. Also, another probe 244 (Probe 2/3) includes an oligonucleotide 246 capable of binding to a sequence region present in Target 2 and another sequence region present in Target 3.

Example 6

Increasing Multiplex Levels in Digital Amplification without Additional Detection Channels This example describes an exemplary approach for increasing the multiplex level of a multiplexed digital amplification assay.

A. Introduction

The ability to measure multiple targets simultaneously (multiplexing) within every partition of a digital amplification system is often limited by the detection approach. Commonly one measures fluorescence to classify partitions as positive (if the measured fluorescence is high) or negative (if the measured fluorescence is low). Some chemistries, such as TaqMan, allow measurements of several targets simultaneously by utilizing target-specific probes labeled with different dyes. If the detector can measure the fluorescence emitted by R different dyes, then the digital amplification system is effectively capable of measuring R different targets. Typically, instruments that are capable of detecting more colors are more expensive than those with fewer colors. Increasing the number of detectable dyes is expensive and is impractical beyond a certain number. On the other hand, many applications especially where sample is limited could benefit greatly from higher degrees of multiplexing.

This example presents an approach that, given an instrument capable of detecting multiple colors, can dramatically increase the number of simultaneously measured targets without requiring any changes to the detection optics of the instrument. The standard approach of designing assays is that a given target is assessed based on fluorescence produced from a single probe with a single dye. Thus, if the instrument is capable of detecting two colors, such as the light emitted from the dyes FAM and VIC, one measures the concentration of one target by counting the number of partitions with positive FAM signals and another target by counting the number of partitions with positive VIC signals.

One can design assays that produce fluorescence on multiple channels simultaneously. If processed on a digital amplification platform with a large number of partitions these assays can be multiplexed together with single channel assays and can be measured by counting the number of partitions with fluorescence on both channels.

B. Example with Two-color FAM-VIC Detection

Assuming we are looking at two unlinked loci (target 1 and target 2), and given some number of FAM-only positive droplets as well as some number of VIC-only positive droplets, we can estimate how many FAM-VIC double-positive droplets we expect. If we are operating at low concentrations this number should be small and can be worked out in a straightforward fashion.

If we set up a third assay (target 3) such that it has two additional probes—one labeled with FAM and one labeled with VIC, we can estimate the concentration of this third target locus by how many excess FAM-VIC double-positive droplets we have compared to the expectation. This would reduce the overall precision, but not much, and basically not at all if we are operating in a dilute regime (i.e., the total number of droplets is much larger than the number of positive droplets). Below is an example of an algorithm that can be used to determine the concentration of the excess FAM-VIC double positive droplets (or other partitions).

The use of multiple probes labeled with the same dye will increase the fluorescence of the negative droplets, which can present a challenge in extreme cases if fluorescence of the negative droplets starts approaching that of the positive droplets. This challenge can be addressed effectively by using sufficiently robust assays. One can also use common probes (e.g., see Examples 3-5) and avoid the elevation of negative fluorescence altogether. For the above example, we can consider using a common FAM probe for target 1 and target 3 and a common VIC probe for target 2 and target 3 by utilizing tailed primers or locked nucleic acid probes.

C. Additional Considerations

One gains an ever-larger advantage from this approach when one uses four or more colors. There are six combinations of two colors if one has four to choose from. Together with single colors, this would give a total of ten reporters. If we go further and use triplets of colors we would end up with 13 reporters.

The advantage of using this multi-color scheme becomes more pronounced with higher numbers of partitions. For that reason, this approach is of particular utility when combined with more recent implementations of digital amplification such as digital PCR in droplets where thousands or millions of partitions can be produced in an easy and cost effective manner.

Several assay schemes can be employed to assess a target with multiple colors simultaneously. One could design a multi-labeled probe—e.g., a single probe can be labeled with both FAM and VIC on the same molecule (e.g., see FIG. 6). As another example, the same oligonucleotide may be labeled separately with FAM and VIC, to produce a FAM-labeled version and a VIC-labeled version of the same probe, and then the two versions mixed (e.g., see FIG. 9B). In other cases, such as for a TaqMan assay, two probes can be designed to bind to different regions of the same amplicon strand (e.g., see FIG. 9A). Alternatively, the probes can bind to opposite strands of the amplicon (e.g., see FIG. 10), which may position the dyes away from the quenchers and facilitate the fluorescence increase from the bound probes.

This approach is general and can be used with a range of chemistries including ligation chain reaction, molecular beacons, scorpion probes, molecular inversion probes, or the like.

D. Mathematical Approach for Estimating Excess FAM-VIC Droplets

The following is an example of an algorithm that can be used to estimate concentrations of a joint FAM-VIC species (e.g., target 3 of FIGS. 6-8).

1. Get 2×2 table of FAM versus VIC counts.
2. Compute concentration of distinct FAM and joint FAM-VIC as if there are 1 species.
3. Compute concentration of distinct VIC and joint FAM-VIC as if there are 1 species.
4. Try out different concentrations of joint FAM-VIC (from which the concentration of distinct FAM and distinct VIC can be found), and find the best fit of the probability table (Table 1) with the observed counts.

TABLE 1

|  | FAM− | FAM+ |
| --- | --- | --- |
| VIC+ | $(1-f) v (1-c)$ | $1 -$ sum of others |
| VIC− | $(1-f)(1-v)(1-c)$ | $f(1-v)(1-c)$ |

E. MATLAB Implementation of the Algorithm

Below is an example of a MATLAB implementation of the algorithm. Note that the algorithm can be expanded in a straightforward fashion to high order multiplexes.

```
% Consider three types of DNA fragments: Fam-Vic together,
% Fam fragment, Vic fragment. We observe some probabili-
    ties (counts in
% FAM-VIC cross plot), and the goal is to infer the concen-
    trations.
% First let us do forward. Given concentrations, compute
    counts. Then to do
% inverse, we simply try out different values of concentra-
    tions and select
% one which gives actual counts.
N=20000;
A=10000;
B=20000;
AB=10000; % Joined together
cA=A/N;
cB=B/N;
cAB=AB/N;
fprintf(1, '% f % f % fn', cAB, cA, cB);
pA=1−exp(−cA);
pB=1−exp(−cB);
```

```
pAB=1-exp(-cAB);
% A is X and B is Y in cross plot
p(2,1)=(1-pA)*(1-pB)*(1-pAB); % Bottom left
p(2,2)=pA*(1-pB)*(1-pAB); % Bottom right
p(1,1)=(1-pA)*pB*(1-pAB); % Top Left
p(1,2)=1-p(2,1)-p(2,2)-p(1,1); % Top Right
disp(round(p*N));
% Also compute marginals directly
cAorAB=(A+AB)/N; %=c_A+c_AB;
cBorAB=(B+AB)/N; %=c_B+c_AB;
pAorAB=1-exp(-cAorAB); % Can be computed from p too
pBorAB=1-exp(-cBorAB);
% Inverse
H=p*N; % We are given some hits
% H=[08000; 20000];
% Compute prob
estN=sum(H(:));
i_p=H/estN;
i_pAorAB=i_p(1,2)+i_p(2,2);
i_pBorAB=i_p(1,1)+i_p(1,2);
i_cAorAB=-log(1-i_pAorAB);
i_cBorAB=-log(1-i_pBorAB);
maxVal=min(i_cAorAB, i_cBorAB);
delta=maxVal/1000;
errArr=[ ];
gcABArr=[ ];
forgcAB=0:delta:maxVal
gcA=i_cAorAB-gcAB;
gcB=i_cBorAB-gcAB;
gpA=1-exp(-gcA);
gpB=1-exp(-gcB);
gpAB=1-exp(-gcAB);
gp(2,1)=(1-gpA)*(1-gpB)*(1-gpAB); % Bottom left
gp(2,2)=gpA*(1-gpB)*(1-gpAB); % Bottom right
gp(1,1)=(1-gpA)*gpB*(1-gpAB); % Top Left
gp(1,2)=1-gp(2,1)-gp(2,2)-gp(1,1); % Top Right
gH=gp*estN;
err=sqrt(sum((H(:)-gH(:)).^2));
errArr=[errArr; err];
gcABArr=[gcABArr; gcAB];
end
figure, plot(gcABArr, errArr);
minidx=find(errArr==min(errArr(:)));
minidx=minidx(1);
estAB=gcABArr(minidx);
estA=i_cAorAB-estAB;
estB=i_cBorAB-estAB;
fprintf(1, '% f % f % f\n', estAB, estA, estB);
gpA=1-exp(-estA);
gpB=1-exp(-estB);
gpAB=1-exp(-estAB);
gp(2,1)=(1-gpA)*(1-gpB)*(1-gpAB); % Bottom left
gp(2,2)=gpA*(1-gpB)*(1-gpAB); % Bottom right
gp(1,1)=(1-gpA)*gpB*(1-gpAB); % Top Left
gp(1,2)=1-gp(2,1)-gp(2,2)-gp(1,1); % Top Right
gH=gp*estN;
disp(round(gH));
% Confirm the results using simulation
numMolA=round(estA*estN);
numMolB=round(estB*estN);
numMolAB=round(estAB*estN);
A=unique(randsample(estN, numMolA, 1));
B=unique(randsample(estN, numMolB, 1));
AB=unique(randsample(estN, numMolAB, 1));
U=1:estN;
notA=setdiff(U, A);
notB=setdiff(U, B);
notAB=setdiff(U, AB);
AorBorAB=union(A, union(B, AB));
none=setdiff(U, AorBorAB);
simcount(2,1)=length(none);
simcount(2,2)=length(intersect(A, intersect(notB, notAB)));
simcount(1,1)=length(intersect(B, intersect(notA, notAB)));
simcount(1,2)=length(AorBorAB)-simcount(2,2)-simcount(1,1);
disp(simcount);
```

Example 7

Algorithm for Computation of DNA Fragmentation or for Digital Amplification Multiplexing This example describes an exemplary algorithm to compute a level of DNA fragmentation and/or levels of target in a multiplexed amplification assay.

A. Introduction

1. Totally Fragmented Targets

Figure 14:
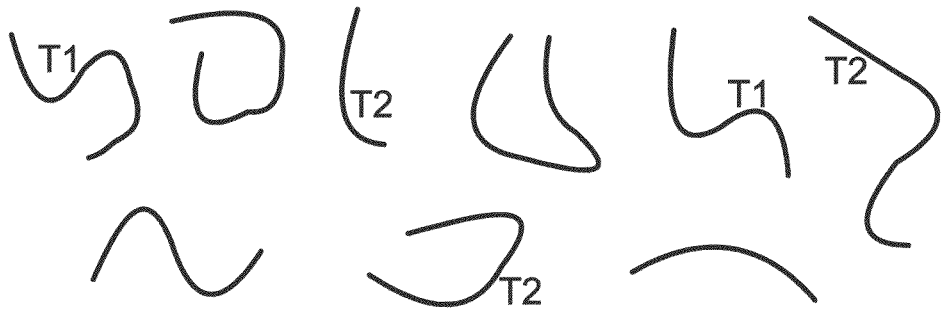
FIG. 14 is a schematic view of a population of fragments containing a pair of unlinked targets, T1 and T2, in accordance with aspects of the present disclosure.

Consider two DNA targets T1 and T2 corresponding to two dyes FAM and VIC, respectively. Let T1 and T2 be always on separate DNA fragments, as illustrated schematically in FIG. 14. Let the number of DNA fragments with T1 and T2 targets be M1 and M2, respectively.

Let the counts of FAM and VIC positive partitions be N1 and N2, respectively. Note that N1 and N2 will be smaller than M1 and M2, respectively, as there can be multiple DNA fragments in a partition. Let the total number of partitions be N. We will refer to digital amplification partitions simply as partitions. In this case, we can expect to see the counts of partitions listed in Table 2.

TABLE 2

|  | VIC Negative | VIC positive | Total |
| --- | --- | --- | --- |
| FAM Positive | N1 · (N − N2)/N | N1 · N2/N | N1 |
| FAM Negative | (N − N1) · (N − N2)/N | (N − N1) · N2/N | N − N1 |
| Total | N − N2 | N2 | N |

If we denote the probability of seeing a partition to be FAM positive as p1=N1/N, and of seeing a partition to be VIC positive as p2=N2/N, then the probability table is given by Table 3.

TABLE 3

|  | VIC Negative | VIC positive | Probability |
| --- | --- | --- | --- |
| FAM Positive | p1 · (1 − p2) | p1 · p2 | p1 |
| FAM Negative | (1 − p1) · (1 − p2) | (1 − p1) · p2 | 1 − p1 |
| Probability | 1 − p2 | p2 | 1 |

In this case, we can say that 100% fragmentation exists.

We can compute the number of T1 and T2 molecules, M1 and M2, respectively as follows, wherein (where $\log = \log_e$):

$$M1 = -N \log(1-p1)$$

$$M2 = -N \log(1-p2)$$

(Given N digital partitions in which P are positive, the number of molecules is $M = -N \log(1 - P/N)$.)

2. No Fragmentation

Figure 15:
FIG. 15 is a schematic view of a population of fragments taken as in FIG. 14, but with the pair of targets always linked to each other on the same individual fragments, in accordance with aspects of the present disclosure.

Now consider the other extreme. Both targets T1 and T2 are always found together on the same DNA fragments (e.g., see FIG. 15). They are linked, perhaps because their loci are quite close to each other on the same part of a chromosome, and fragmentation of the chromosome during DNA isolation did not separate the loci. Therefore, N1=N2. The expected counts and probabilities are listed in Tables 4 and 5, respectively.

TABLE 4

|  | VIC Negative | VIC positive | Total |
|---|---|---|---|
| FAM Positive | 0 | N1 | N1 |
| FAM Negative | N − N1 | 0 | N − N1 |
| Total | N − N1 | N1 | N |

TABLE 5

|  | VIC Negative | VIC positive | Probability |
|---|---|---|---|
| FAM Positive | 0 | p1 | p1 |
| FAM Negative | (1 − p1) | 0 | 1 − p1 |
| Probability | 1 − p1 | p1 | 1 |

In this case, we can say that 0% fragmentation exists.

We can compute the number of T1 and T2 molecules as follows, where $p1=N1/N$:

$$M1 = -N \log(1-p1)$$

$$M2 = -N \log(1-p1)$$

3. Partial Fragmentation

Figure 16:
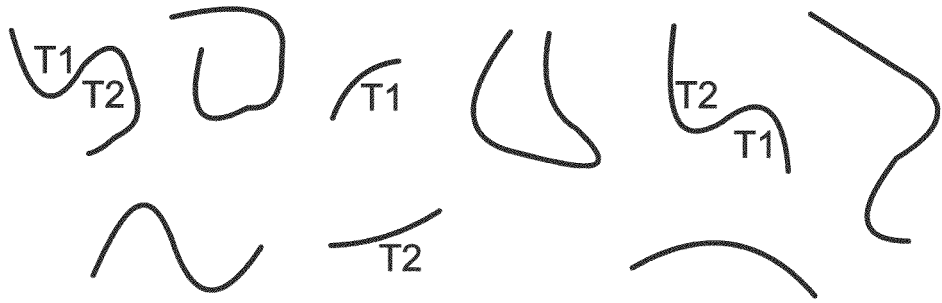
FIG. 16 is a schematic view of a population of fragments taken as in FIG. 14, but with the pair of targets only partially linked to each other within the population, in accordance with aspects of the present disclosure.

In the intermediate situation, where the targets are together on some fragments, but also happen to be on separate fragments, then we have partial fragmentation (e.g., see FIG. 16).

Suppose we have M3 molecules of linked T1 and T2 fragments, M1 molecules of separate T1 fragments, and M2 molecules of separate T2 fragments.

We can make a table of counts of partitions (Table 6).

TABLE 6

|  | VIC Negative | VIC positive | Total |
|---|---|---|---|
| FAM Positive | N01 | N11 | N1 |
| FAM Negative | N00 | N10 | N − N1 |
| Total | N − N2 | N2 | N |

4. Problem Statement

How can we find the number of molecules M1, M2 and M3, and thereby getting extent of fragmentation? For example if M1=M2=M3, then we would say that there is 50% fragmentation, as 50% of linked molecules got fragmented into separate fragments and 50% remained intact.

B. Multiplexing of PCR to Many Targets Using Few Colors

We have an algorithm that provides a solution to the above problem, and there is another interesting application for the algorithm. With this algorithm and by using a FAM probe for target T1, a VIC probe for target T2, and both FAM and VIC probes placed close to each other for target T3, we can achieve multiplexing of 3 targets by using 2 colors. Basically, we get a third color for "free" using the algorithm.

Now consider the case if there are 3 dyes. Thus, we will have a 2×2×2 table of 8 observed counts.

There are seven different kinds of targets: T1, T2, T3, T12, T23, T13, and T123. Here, for example, T12 means a target that is amplified to produce an amplicon bound by Dye 1 and Dye 2 probes, and T123 means a target that is amplified to produce an amplicon bound by one or more probes containing all three dyes, and likewise for the others.

If we have 4 dyes, then we have $2^4=16$ counts, and we can now multiplex quantitation of $2^4-1=15$ target genes. In general, with R colors, we have $2^R$ observed counts and we can have $2^R-1$ targets.

C. Solution for 2 Dyes and 3 Targets

Suppose we are given the counts listed in Table 7.

TABLE 7

|  | VIC Negative | VIC positive | Total |
|---|---|---|---|
| FAM Positive | N01 | N11 | N1 |
| FAM Negative | N00 | N10 | N − N1 |
| Total | N − N2 | N2 | N |

Consider the following three cases:
1. We turn off VIC, as if VIC cannot be seen at all.
2. We turn off FAM, as if FAM cannot be seen at all.
3. We consider both FAM and VIC as if they are only one color.

We will have the following three observations:
1. Turning off VIC: We will be able to see T1 or T12, together and indistinguishably, as if there were one target. It gives the total number of molecules of T1 and T12, as if there were one target species.
2. Turning off FAM: We will be able to count T2 or T12, indistinguishably, as if there were one target. It gives the total number of molecules of T2 and T12, as if there were one target species.
3. Considering both FAM and VIC indistinguishably: We will be able to count T1, T2, or T12, indistinguishably. It gives the total number of molecules of T1, T2, and T12, as if there were one target species.

This allows us to step 3 equations in 3 unknowns. We can show these three cases in the form of a table.

TABLE 8

| Visible Dyes | Invisible Dyes | Distinct Dyes | Indistinct Dyes | Target Detected | Positive Count | Molecules |
|---|---|---|---|---|---|---|
| FAM | VIC | — | — | {T1, T12} | N1 | $-\log(1 - N1/N)$ |
| VIC | FAM | — | — | {T2, T12} | N2 | $-\log(1 - N2/N)$ |
| FAM, VIC | — | — | {FAM, VIC} | {T1, T2, T12} | N01 + N10 + N11 | $-\log(1 - (N01 + N10 + N11)/N)$ |

The three linear equations in three unknowns M1, M2 and M12 are:

$$\begin{bmatrix} 1 & 0 & 1 \\ 0 & 1 & 1 \\ 1 & 1 & 1 \end{bmatrix} \begin{bmatrix} M1 \\ M2 \\ M12 \end{bmatrix} = \begin{bmatrix} M_{1\ or\ 12} \\ M_{2\ or\ 12} \\ M_{1\ or\ 2\ or\ 12} \end{bmatrix} = \begin{bmatrix} -N\log\left(1 - \frac{N1}{N}\right) \\ -N\log\left(1 - \frac{N2}{N}\right) \\ -N\log\left(1 - \frac{N01 + N10 + N11}{N}\right) \end{bmatrix}$$

We solve the above equations to get values of M1, M2, and M12.

We can then compute the extent of fragmentation in % as follows:

$$M = (M1+M2)/2$$

$$F = M/(M+M12)*100$$

D. Algorithm Steps

Now we write down the steps of the algorithm clearly using the input of Table 9.

TABLE 9

|  | VIC Negative | VIC positive | Total |
|---|---|---|---|
| FAM Positive | N11 | N12 | N1 |
| FAM Negative | N21 | N22 | N − N1 |
| Total | N − N2 | N2 | N |

Algorithm:

Step 1. Compute the three entities:

$$M_{1or12} = -N \cdot \log(1 - N1/N)$$

$$M_{2or12} = -N \cdot \log(1 - N2/N)$$

$$M_{1or2or12} = -N \cdot \log(1 - (N01+N10+N11)/N)$$

Step 2. Solve the following linear equations:

$$\begin{bmatrix} 1 & 0 & 1 \\ 0 & 1 & 1 \\ 1 & 1 & 1 \end{bmatrix} \begin{bmatrix} M1 \\ M2 \\ M12 \end{bmatrix} = \begin{bmatrix} M_{1\,or\,12} \\ M_{2\,or\,12} \\ M_{1\,or\,2\,or\,12} \end{bmatrix} = \begin{bmatrix} -N\log\left(1 - \frac{N1}{N}\right) \\ -N\log\left(1 - \frac{N2}{N}\right) \\ -N\log\left(1 - \frac{N01+N10+N11}{N}\right) \end{bmatrix}$$

Step 3. Compute extent of fragmentation.

$$M = (M1+M2)/2$$

$$F = M/(M+M12)*100$$

Step 4. Compute confidence intervals based on the concentration and expected number of positive counts. To compute confidence interval of F, we note that it is ratio of two random variables. Then we apply techniques to estimate confidence interval of ratio of two random variables for F.

The output is M1, M2, and F and their confidence intervals.

E. Outline of an Alternative Solution

Now we present an alternative solution to the problem of partial fragmentation phrased in terms of optimization of an objective criterion. First let us make the following table. Depending upon what type of molecules we have in a partition we will have corresponding FAM and VIC colors of the partition.

Table 10 maps molecules into partition colors.

TABLE 10

| Presence of Molecules in a Partition | | | Partition Color | |
|---|---|---|---|---|
| T1 | T2 | T12 | FAM (T1) | VIC (T2) |
| 0 | 0 | 0 | Neg | Neg |
| 0 | 1 | 0 | Neg | Pos |
| 1 | 0 | 0 | Pos | Neg |
| 0 | 0 | 1 | Pos | Pos |
| 0 | 1 | 1 | | |
| 1 | 0 | 1 | | |
| 1 | 1 | 0 | | |
| 1 | 1 | 1 | | |

Suppose we make a "guess" of M1, M2, and M12. We can compute the probabilities of a partition having a copy of the T1, T2, or T12 target using inverse equations:

$$p12 = 1 - \exp(-M12/N)$$

$$p1 = 1 - \exp(-M1/N)$$

$$p2 = 1 - \exp(-M2/N).$$

From these probabilities we can compute the predicted counts as shown in Table 11.

TABLE 11

|  | VIC Negative | VIC positive |
|---|---|---|
| FAM Positive | $p1(1 - p2)(1 - p12)N$ | $(1 - \text{(sum of other 3 cells in this table)})N$ |
| FAM Negative | $(1 - p1)(1 - p2)(1 - p12)N$ | $(1 - p1)p2(1 - p12)N$ |

The probabilities above can be filled using Table 10, which maps presence of molecules into partition colors.

If our "guess" is really correct, then the predicted counts will "match" closely with our expected counts. Thus an optimization algorithm under the above objective criterion that needs to be minimized could also be used to solve the problem.

M1, M2, M12 = best guess = least deviation of predicted counts and actual counts We can then compute the extent of fragmentation in % as follows:

$$M = (M1+M2)/2$$

$$F = M/(M+M12)*100.$$

F. Solution for 3 Dyes and 7 Targets

To solve the problem for greater number of dyes, we need more equations as there are more unknowns. For 3 dyes and 7 targets, we need 7 equations to find the concentration of these 7 targets.

We have Table 12 with $2^3 = 8$ rows of counts of partitions depending upon which dyes are positive.

Denote the three dyes by D1, D2 and D3.

TABLE 12

| Presence of color in a partition | | | |
|---|---|---|---|
| D1 | D2 | D3 | Count of Partitions |
| Neg | Neg | Neg | N000 |
| Neg | Pos | Neg | N010 |
| Pos | Neg | Neg | N100 |
| Neg | Neg | Pos | N001 |
| Neg | Pos | Pos | N011 |
| Pos | Neg | Pos | N101 |
| Pos | Pos | Neg | N110 |
| Pos | Pos | Pos | N111 |
| | Total | | N |

Consider Table 13.

TABLE 13

| Visible Dyes | Invisible Dyes | Distinct Dyes | Indistinct Dyes | Target Detected | Positive Count |
|---|---|---|---|---|---|
| D1, D2, D3 | — | — | {D1, D2, D3} | {T1, T2, T3, T12, T13, T23, T123} | C1 = N − N000 |

TABLE 13-continued

| Visible Dyes | Invisible Dyes | Distinct Dyes | Indistinct Dyes | Target Detected | Positive Count |
|---|---|---|---|---|---|
| D1 | D2, D3 | — | — | {T1, T12, T13, T123} | C2 = N100 + N101 + N110 + N111 |
| D2 | D1, D3 | — | — | {T2, T12, T23, T123} | C3 = N010 + N011 + N110 + N111 |
| D3 | D1, D2 | — | — | {T3, T13, T23, T123} | C4 = N001 + N011 + N101 + N111 |
| D1, D2 | D3 | D1, D2 | — | {T1, T13} | Compute concentration $M_{1 or 13}$ by solving 2 dye problem* |
| D1, D3 | D2 | D1, D3 | — | {T1, T12} | Compute concentration $M_{1 or 12}$ by solving 2 dye problem* |
| D2, D3 | D1 | D2, D3 | — | {T2, T12} | Compute concentration $M_{2 or 12}$ by solving 2 dye problem* |

*Note that for row 5, we could have also detected {T2, T23} or {T12, T123}, and for row 6, {T3, T23}, and for row 7, {T3, T13} and {T23, T123}. This choice does not matter and all lead to the same results.

We make 3 recursive calls, in rows 5, 6 and 7.

For example, in row 5, we are really solving 2 dyes, D1 and D2, case with 3 targets: {T1, T13} as one target, {T2, T23} as second target, and {T12, T123} as third linked target.

Similarly, in rows 6 and 7, we make recursive calls to solve the simpler problem of 2 dyes and 3 targets.

The system of equation looks like as follows:

$$\begin{bmatrix} 1111111 \\ 1001101 \\ 0101011 \\ 0010111 \\ 1000100 \\ 1001000 \\ 0101000 \end{bmatrix} \begin{bmatrix} M1 \\ M2 \\ M3 \\ M12 \\ M13 \\ M23 \\ M123 \end{bmatrix} = \begin{bmatrix} M_{all} \\ M_{1\ or\ 12\ or\ 13\ or\ 123} \\ M_{2\ or\ 12\ o\ 23\ or\ 123} \\ M_{3\ or\ 13\ or\ 23\ or\ 123} \\ M_{1\ or\ 13} \\ M_{1\ or\ 12} \\ M_{2\ or\ 12} \end{bmatrix} = \begin{bmatrix} -N\log\left(1 - \frac{C1}{N}\right) \\ -N\log\left(1 - \frac{C2}{N}\right) \\ -N\log\left(1 - \frac{C3}{N}\right) \\ -N\log\left(1 - \frac{C4}{N}\right) \\ \text{Recursive call} \\ \text{Recursive call} \\ \text{Recursive call} \end{bmatrix}$$

The above system of linear equations can be solved to find concentrations of 7 targets.

G. R Dyes and $2^R - 1$ Targets

Now we give the steps to generalize the algorithm to an arbitrary number of dyes.

This is a recursive algorithm. Since we have a solution for the case when R=2, we can solve for any number of R through recursion.

Input:

For R dyes, we are given a table of counts of partitions which has $2^R$ rows, for all possible combinations of presence or absence of colors in a partition.

Algorithm:

Step 1. Set up a system of $2^R - 1$ linear equations. To obtain these equations consider different ways of making some colors invisible. Also consider the case when all colors are indistinguishable, which gives the first row. It can be shown that we can obtain $2^R - 1$ equations in $2^R - 1$ target concentrations (unknowns). When we make certain colors invisible, then we reduce the problem to a case with fewer colors, which can be solved recursively, all the way down to case when there are 2 dyes and 3 targets.

Step 2. Solve the equations.

Step 3. Compute confidence intervals based on the concentration and expected number of positive counts.

Output:

Concentrations of $2^R - 1$ targets along with confidence intervals.

Example 8

Multi-Labeled Probes

This example describes exemplary multi-labeled probes and methods of using the probes in a multiplexed digital amplification assay; see FIGS. 17-22. The multi-labeled probes may be utilized for the color-based multiplexed assays described in Section I and in Examples 6 and 7. Alternatively, or in addition, the multi-labeled probes may be utilized for intensity-based multiplexing, as described in U.S. Provisional Patent Application Ser. No. 61/507,082, filed Jul. 12, 2011; and U.S. Provisional Patent Application Ser. No. 61/510,013, filed Jul. 20, 2011, which are incorporated herein by reference.

Typical 5' nuclease assay (TaqMan) probes have a single fluorophore and a quencher, or two fluors where the second fluor acts to quench the first fluorophore through FRET (e.g., a TAMRA "quencher"). The fluorophore and quencher are typically attached to the 5'- and 3'-most bases/nucleotides of the oligonucleotide probe.

Oligonucleotide synthesis chemistry allows fluorophores to be added to internal nucleotides/bases of a probe. Attaching multiple fluorophores to one oligonucleotide probe allows creation of a wider range of probes, which can be used to enhance multiplexing capabilities. The ability to put multiple fluors on one probe allows the resulting emission fluorescence to be "tuned" to achieve more fluorescence signatures than are possible through single fluorophores. Probe spectra will generally be a composite result of the multiple fluorophores included. For fluorophores that can resonate or otherwise interact, the proximity of the fluorophores and location (internal or end label) will allow additional tuning possibilities. It is not necessary that the multiple fluorophores (or quenchers) be different. Addition of multiple molecules of the same fluor also may allow different fluorescence output on a per-probe basis. For some applications, it may be beneficial to put the quencher on the 5'-end of the oligonucleotide so that probe degradation removes the quencher, but leaves the other fluorophores attached on the remaining portion of the oligonucleotide. That way, when the quencher is cleaved off, the same signal is obtained from the probe, but each probe could have a different signature (e.g., probe 1—FAM; probe 2—FAM+Cy3; probe 3—FAM+HEX; probe 4—FAM+FAM; etc.).

The approach is also applicable to multiplexing for other target molecules. Although detection of target nucleic acids is clearly an area of great interest, it is also possible to apply this concept to other types of probes (for example, antibody probes for protein targets).

Figure 17:
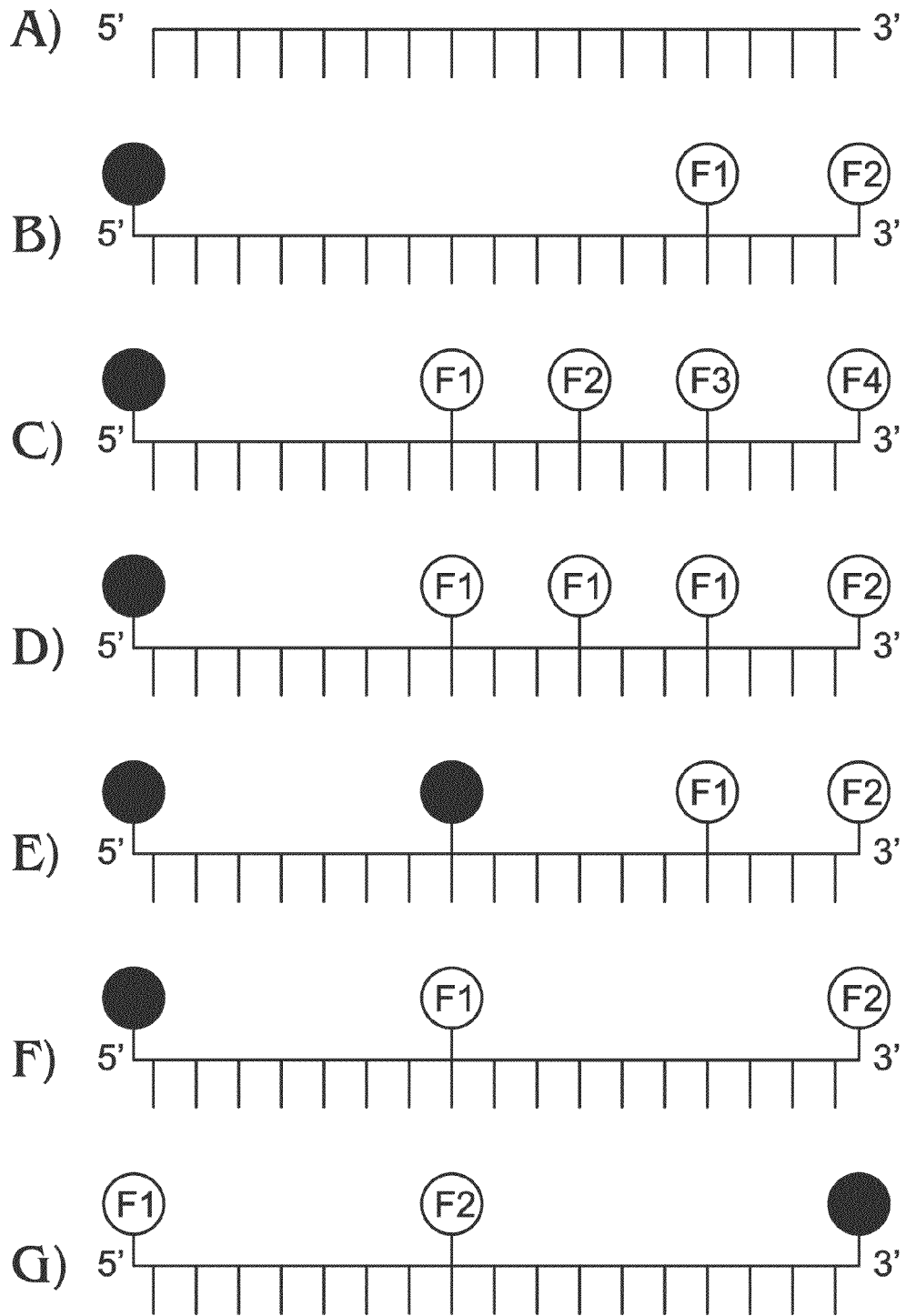
FIG. 17 is a schematic representation of a set of exemplary multi-labeled probes for use in digital amplification assays, in accordance with aspects of the present disclosure.

FIG. 17 show a schematic representation of an unlabeled oligonucleotide (A) and a set of exemplary multi-labeled probes (B-G) containing the oligonucleotide. Each solid circle and open circle represents a quencher (also termed a quencher moiety) and a fluorophore, respectively, attached to the oligonucleotide. F1 to F4 identify structurally distinct fluorophores. The oligonucleotide may have any suitable length, such as 5 to 500, 10 to 200, or 15 to 100 nucleotides, among others.

The multi-labeled probes of FIG. 17 are as follows: B) oligonucleotide with a 5' quencher and fluorophores (F1 and F2) at respective internal and 3'-end positions; C) oligonucleotide with a 5' quencher moiety and fluorophores (F1 to F4) at 3' and multiple internal positions; D) oligonucleotide with a 5' quencher moiety and fluorophores (3×F1, F2) at 3' and multiple internal positions; E) oligonucleotide with a 5' quencher moiety and an internal quencher moiety plus fluorophores at 3' and internal positions; F) oligonucleotide with a 5' quencher moiety and fluorophores at 3' and internal positions, with greater separation between fluorophores; and G) oligonucleotide with fluorophores at the 5'-end and an internal position and a quencher at the 3'-end position.

Figure 18:
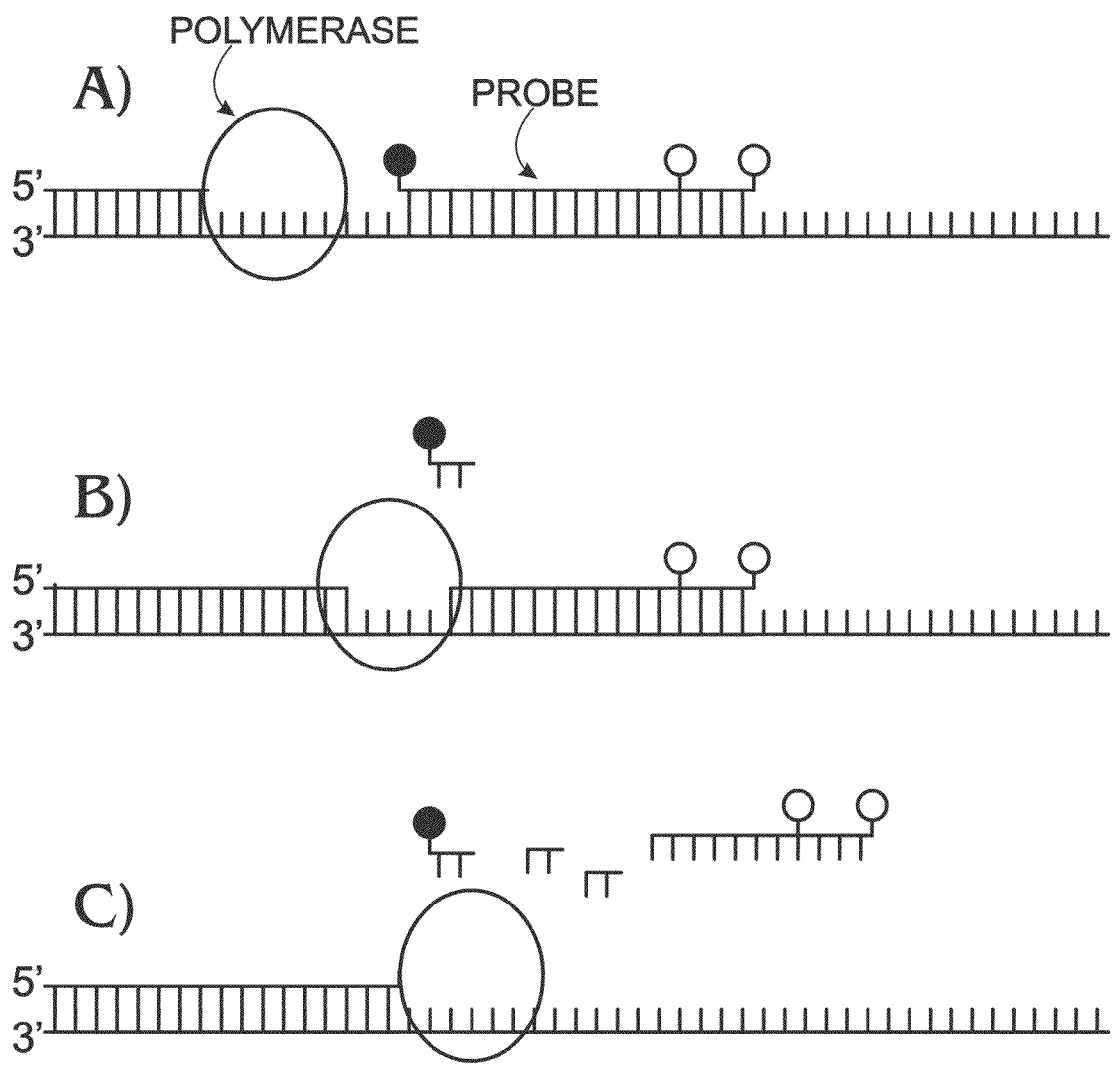
FIG. 18 is a schematic illustration of a template molecule being copied by DNA polymerase during target amplification in the presence of a multi-labeled probe molecule and depicting probe degradation by the polymerase to separate a quencher from fluorophores of the probe molecule, in accordance with aspects of the present disclosure.

FIG. 18 depicts separation of the quencher and fluorophores of a probe molecule during target amplification. A template molecule is shown being copied (complementarily) by DNA polymerase in the presence of an exemplary multi-labeled probe molecule (FIG. 17B). A) Polymerase is extending a nucleic acid strand upstream of a probe binding site. B) 5' nuclease activity of the polymerase removes the 5'-most nucleotides (including the quencher in this example) from the probe, allowing the quencher and fluorophores to be spatially separated. C) Polymerase continues to remove 5' nucleotides from the probe until binding of the probe becomes unstable and the remaining probe fragment dissociates from the template strand. Multiple fluorophores still may be connected to each other in the probe fragment, but are separated from the quencher.

Figure 19:
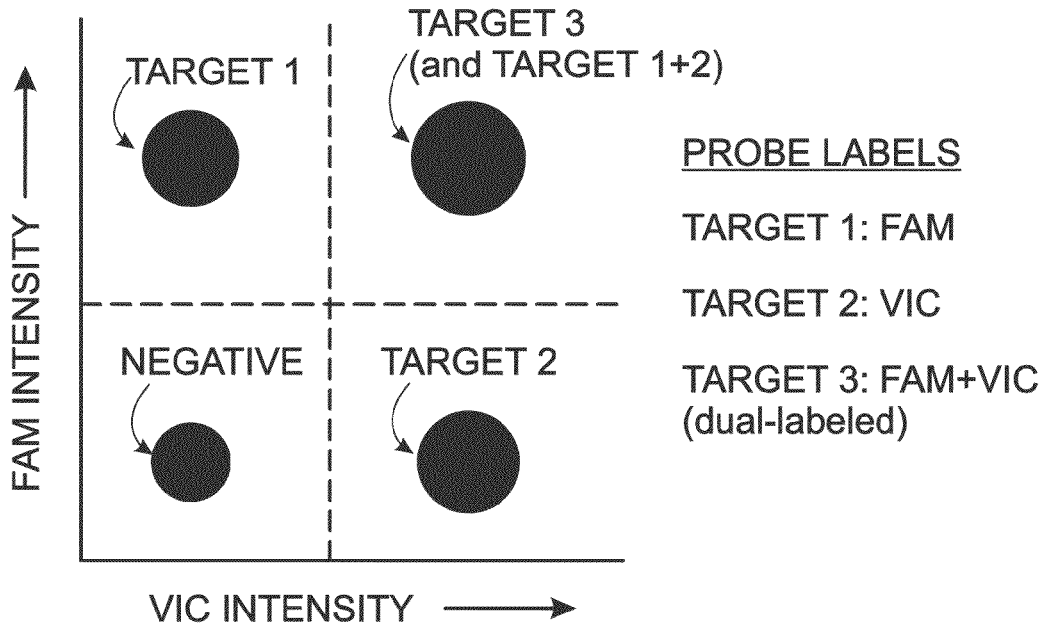
FIG. 19 is an exemplary two-dimensional histogram of droplet intensities, showing clusters that may be obtained in a multiplexed digital amplification assay for three targets performed with a combination of single-labeled and dual-labeled probes each labeled with FAM, VIC, or both FAM and VIC, in accordance with aspects of the present disclosure.

FIG. 19 shows an exemplary two-dimensional histogram of droplet intensities, showing droplet clusters that may be obtained in a multiplexed digital amplification assay for three targets performed with a combination of single-labeled and dual-labeled probes each labeled with FAM, VIC, or both FAM and VIC. Here, the droplet cluster produced by target-3 positives is not resolved from droplets double-positive for both target 1 and 2.

Figure 20:
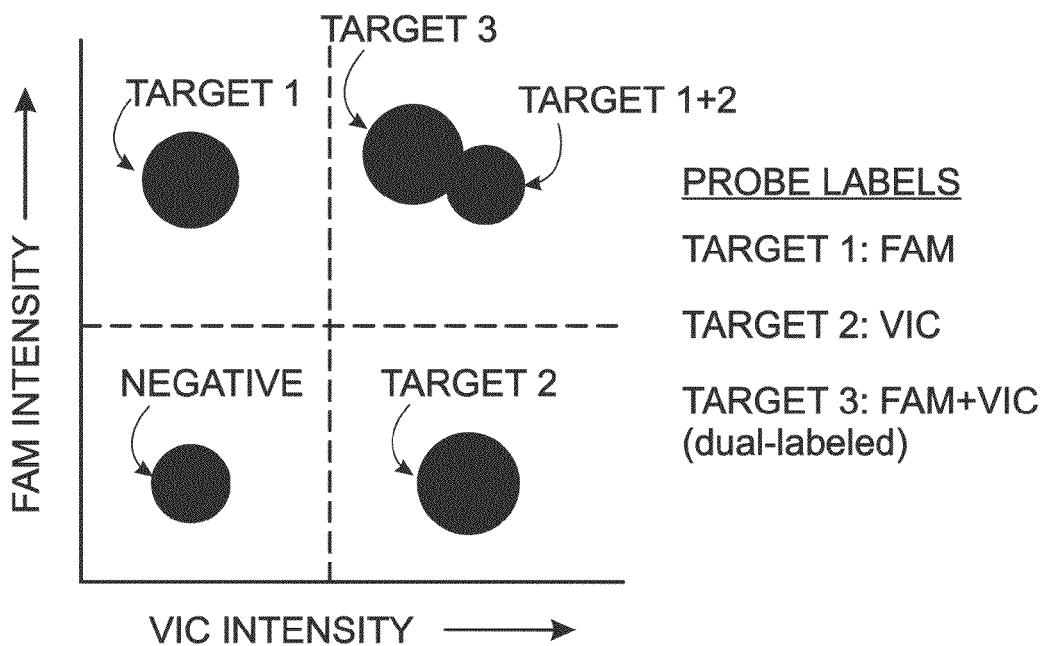
FIG. 20 is another exemplary two-dimensional histogram of droplet intensities, showing clusters that may be obtained in the assay of FIG. 19, with partial resolution of the cluster for target-1+2-positive droplets from the cluster for target-3-positive droplets, in accordance with aspects of the present disclosure.

FIG. 20 shows another exemplary two-dimensional histogram of droplet intensities that may be obtained in the assay of FIG. 19, with partial resolution of a cluster for target-1+2-positive droplets from a cluster for target-3-positive droplets.

Detector optics, particularly excitation sources and optical filters, may be selected to optimize the separation of clusters. For example, two clusters might be substantially overlapping (hard to separate) at a first wavelength condition but substantially non-overlapping at a second wavelength condition. Detectors with spectrophotometer gratings or exchangeable filter sets could provide greater flexibility in wavelength selection.

Figure 21:
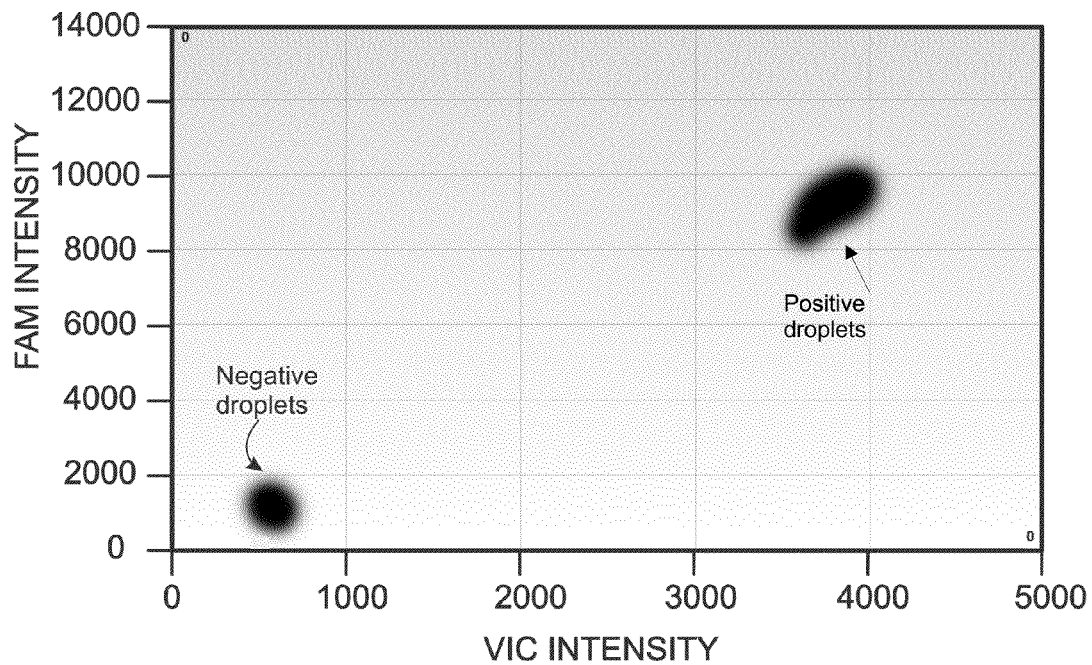
FIG. 21 is an exemplary two-dimensional intensity histogram of droplet intensities, showing clusters that may be obtained in a digital amplification assay performed with only a multi-labeled FAM, VIC probe, in accordance with aspects of the present disclosure.

FIG. 21 shows an exemplary two-dimensional histogram of droplet intensities, illustrating two clusters of data points that may be obtained in a digital amplification assay performed with only a multi-labeled probe.

Figure 22:
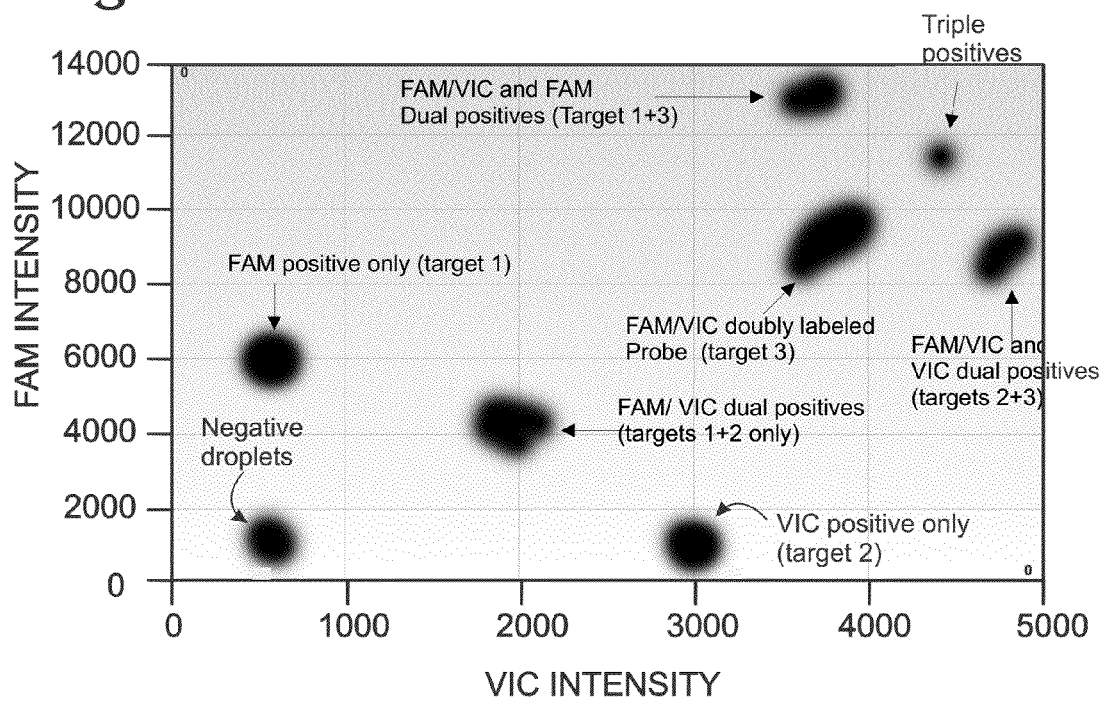
FIG. 22 is another exemplary two-dimensional intensity histogram of droplet intensities, showing clusters that may be obtained in a digital amplification assay performed as in FIG. 21, but with the assay supplemented with pair of single-labeled FAM or VIC probes in addition to the multi-labeled FAM, VIC probe, in accordance with aspects of the present disclosure.

FIG. 22 shows another exemplary two-dimensional histogram of droplet intensities, illustrating various clusters of data points that may be obtained in a digital amplification assay performed as in FIG. 21, but with the assay supplemented with a pair of single-labeled probes (for measuring target 1 and target 2 amplification), in addition to the multi-labeled probe (for measuring target 3 amplification). Putting multiple fluors on the same oligonucleotide can be more advantageous when combined with different levels of probe and/or with different fluors that have different spectral overlap in two (or more) detection channels. The example of FIG. 22 shows the dual fluor probe having slightly higher fluorescence than the FAM-only and VIC-only probes, but it could be either higher or lower (or the same). If about the same (or not), the color-based multiplexing approach disclosed herein may be utilized advantageously to determine average target levels.

Several chemistries can yield the multi-labeled probes disclosed herein, including labeled deoxynucleotides, click chemistry, and various other linker chemistries. The probes could be produced through custom synthesis by an oligonucleotide supplier. References describing exemplary synthetic routes for internal fluorophore incorporation are listed below and are incorporated herein by reference.

Haralambidis J., Chai M. and Tregear G. W. (1987) Preparation of base-modified nucleosides suitable for non-radioactive label attachment and their incorporation into synthetic oligodeoxyribonucleotides. Nucleic Acids Res. 15, 4857-4876.

Randolph J. B., and Waggoner A. S. (1997) Stability, specificity and fluorescence brightness of multiply-labelled fluorescence DNA probes. Nucleic Acids Research; 25:2923-2929.

Brumbaugh J. A., Middendorf L. R., Grone D. L., and Ruth J. L. Proc. Natl. Acad. Sci. USA 1988; 85:5610-5614.

Singh D., Vijayanti K., Ganesh K. N. (1990) Oligonucleotides, part 5+: synthesis and fluorescence studies of DNA oligomers d(AT) 5 containing adenines covalently linked at C-8 with dansyl fluorophore. Nucleic Acids Res.; 18:3339-3345.

Tae Seok Seo, Zengmin Li, Hameer Ruparel, and Jingyue Ju (2003) Click Chemistry to Construct Fluorescent Oligonucleotides for DNA Sequencing. J. Org. Chem.; 68: 609-612.

Example 9

Selected Embodiments

This example describes selected aspects and embodiments related to digital assays with combinatorial use of signals, presented without limitation as a series of numbered paragraphs. Each of these paragraphs can be combined with one or more other paragraphs, and/or with disclosure from elsewhere in the present disclosure, in any suitable manner. Some of the paragraphs below expressly refer to and further limit other paragraphs, providing without limitation examples of some of the suitable combinations.

A1. A method of performing a digital assay, comprising: (a) creating R signals representative of light detected from each of a plurality of partitions of a sample; and (b) estimating a concentration of more than R different targets in the partitions based on how the R signals vary relative to one another among the partitions.

B1. A method of performing a digital assay for more than R targets, comprising: (a) separating a sample into partitions; (b) creating R signals representative of light detected from the partitions; and (c) estimating a concentration of more than R targets in the partitions based on the R signals.

B2. The method of paragraph B1, wherein at least one of the R signals reports the presence or absence of a target in each partition independently of every other one of the R signals.

B3. The method of paragraph B1 or B2, wherein each of the R signals reports the presence or absence of a different target in each partition independently of every other one of the R signals.

B4. The method of any of paragraphs B1 to B3, wherein a combination of two or more of the R signals collectively reports the presence or absence an R+1 target in each partition.

B5. The method of any of paragraphs B1 to B4, further comprising a step of determining a number of the partitions that are positive for each of the R signals alone and a number that are positive for at least one combination of two or more of the R signals.

B6. The method of paragraph B5, wherein the step of estimating a concentration includes a step of estimating concentrations of each of the more than R targets that collectively correspond to the determined numbers of positives, if each target has a Poisson distribution among the partitions.

B7. The method of any of paragraphs B1 to B6, wherein the step of estimating includes a step of finding solutions to a set of simultaneous equations, and wherein the equations each have the same variables.

B8. The method of paragraph B7, wherein the simultaneous equations are linear equations.

B9. The method of paragraph B7 or B8, wherein the solutions are obtained by numerical analysis.

B10. The method of any of paragraphs B7 to B9, wherein the step of finding solutions includes a step of finding solutions to at least $2^R-1$ equations.

B11. The method of any of paragraphs B7 to B10, wherein each equation is based on copies of each target having a Poisson distribution among the partitions.

B12. The method of any of paragraphs B1 to B11, wherein each of the R signals is a composite signal that includes two or more integral signal portions corresponding to the presence or absence of different targets in individual partitions.

B13. The method of any of paragraphs B1 to B12, wherein the step of separating a sample forms the partitions with an average concentration per partition of less than about one copy of each of the more than R targets.

B14. The method of any of paragraphs B1 to B13, wherein the step of separating a sample forms one or more partitions containing no copies of a target for each of the more than R targets.

B15. The method of any of paragraphs B1 to B14, wherein the partitions are droplets.

B16. The method of any of paragraphs B1 to B15, wherein each of the R signals is representative of fluorescence emission that is detected.

B17. The method of any of paragraphs B1 to B16, further comprising a step of performing an amplification reaction in one or more of the partitions before the step of creating R signals.

B18. The method of paragraph B17, wherein the step of performing an amplification reaction includes a step of thermally cycling partitions.

B19. The method of any of paragraphs B1 to B18, wherein each target is a nucleic acid.

B20. The method of any of paragraphs B1 to B19, wherein the partitions include a first probe reporting a presence or absence of a first target molecule in individual partitions, a second probe reporting a presence or absence of a second target molecule in individual partitions, and at least one third probe reporting a presence or absence of a third target molecule in individual partitions.

B21. The method of claim B20, wherein the at least one third probe is a single third probe.

B22. The method of any of paragraphs B1 to B19, wherein the partitions include a first probe reporting a presence or absence of a first target molecule in individual partitions, a second probe reporting a presence or absence of a second target molecule in individual partitions, and wherein the first and second probes collectively report a presence or absence of a third target molecule in individual partitions.

B23. The method of any of paragraphs B1 to B22, wherein each of the R signals is representative at least predominantly of light detected from a different fluorophore.

B24. The method of any of paragraphs B1 to B23, wherein the partitions all have substantially same volume.

B25. The method of any of paragraphs B1 to B24, wherein at least one of the more than R targets is a linked version of at least two of the other R targets.

C1. A method of performing a digital assay, comprising: (a) separating a sample into partitions, with each partition capable of amplifying more than R targets, if present in the partition; (b) creating R signals representative of light detected from the partitions, wherein, for at least one of the more than R targets, amplification in a partition of the at least one target selectively changes only one of the R signals, and wherein, for at least one other of the more than R targets, amplification in a partition of at least one other target coordinately changes two or more of the signals; and (c) estimating a concentration of each of the more than R targets based on the R signals created.

C2. The method of paragraph C1, wherein the step of amplifying includes a step of thermally cycling the partitions before the step of creating.

C3. The method of paragraph C1 or C2, wherein the R signals are representative of light detected from fluid carrying droplets through an examination region.

C4. The method of any of paragraphs C1 to C3, wherein the step of creating includes a step of creating two or more signals that represent different wavelengths and/or wavelength ranges of detected light.

C5. The method of any of paragraphs C1 to C4, wherein the step of creating includes a step of creating two or more signals that are representative of a same wavelength range of detected light produced by illumination with a different wavelength or wavelength range for each of the two or more signals.

D1. A method of performing a multiplexed digital amplification assay, the method comprising: (a) amplifying more than R targets in partitions; (b) creating R signals representative of light detected in R different wavelength regimes from the partitions, where R≥2; and (c) calculating an average level of each target in the partitions based on the R signals, wherein the level calculated accounts for a coincidence, if any, of different targets in the same individual partitions. For example, if T denotes the number of targets, then T>R.

D2. The method of paragraph D1, wherein amplification of each target is reported by a different signal or combination of the signals than any of the other targets individually.

D3. The method of paragraph D1 or D2, wherein each of the signals reports amplification of a different combination of at least two of the targets.

D4. The method of paragraph D3, wherein the partitions are droplets, further comprising a step of determining a number of droplets exhibiting amplification of any of the at least two targets for each signal, and wherein the step of calculating is based on the number determined for each of the R signals.

D5. The method of any of paragraphs D1 to D4, wherein the step of calculating includes a step of finding solutions to a set of simultaneous equations.

D6. The method of paragraph D5, wherein there are T targets, wherein the step of finding solutions includes a step of finding solutions to T simultaneous equations, and wherein $R<T\le2^R-1$.

D7. The method of paragraph D5 or D6, wherein the solutions are obtained by numerical analysis.

D8. The method of any of paragraphs D1 to D7, wherein there are three targets, and wherein the signals representative of light are detected from two fluorophores associated with probes that bind to amplicons of respective targets during amplification.

D9. The method of paragraph D8, wherein the two fluorophores are VIC and FAM.

D10. The method of paragraph D8 or D9, wherein the partitions contain a first probe for a first of the three targets, a second probe for a second of the three targets, and a third probe for a third of the three targets, and wherein the first probe is labeled exclusively with VIC, the second probe is labeled exclusively with FAM, and the third probe is labeled with both VIC and FAM.

D11. The method of paragraph D10, wherein the third probe includes a FAM-labeled probe that is not labeled with VIC and a VIC-labeled probe that is not labeled with FAM.

D12. The method of any of paragraphs D1 to D11, wherein the average level is a concentration.

D13. The method of any of paragraphs D1 to D12, wherein the step of calculating an average level includes a step of determining a total number of amplification-positive partitions for each type of target and a step of determining a total number of partitions.

D14. The method of any of paragraphs D1 to D13, further comprising a step of distributing copies of the more than R targets among the partitions such that some partitions contain more than one copy of a given target.

D15. The method of any of paragraphs D1 to D13, wherein there are at least four targets.

E1. A method of performing a multiplexed digital amplification assay, the method comprising: (a) amplifying more than R targets in droplets; (b) creating R signals representative of light detected in R different wavelength regimes from the droplets, where $R \geq 2$; and (c) calculating an average level of each of the more than R targets by finding solutions to a series of simultaneous equations. For example, if T denotes the number of targets, then $T>R$.

E2. The method of paragraph E1, wherein amplification of each target is reported by a different signal or combination of the signals than any of the other targets individually.

E3. The method of paragraph E1 or E2, wherein each of the signals reports amplification of a different combination of at least two of the targets.

E4. The method of paragraph E3, further comprising a step of determining a total number of droplets that are amplification-positive for any of the at least two targets reported on by each signal, and wherein the step of calculating is based on the total number determined for each of the R signals.

E5. The method of any of paragraphs E1 to E4, wherein there are T targets, wherein the step of calculating includes a step of finding solutions to T simultaneous equations, and wherein $R<T \leq 2^R - 1$.

E6. The method of any of paragraphs E1 to E5, wherein the solutions are obtained by numerical analysis.

E7. The method of any of paragraphs E1 to E6, wherein the level accounts for any coincidence of different targets in the same individual droplets.

F1. A method of performing a multiplexed digital amplification assay, the method comprising: (a) amplifying more than R targets in droplets; (b) creating R signals representative of light detected in R different wavelength regimes from the droplets, wherein $R \geq 2$ and each of the signals reports amplification of a different combination of at least two of the targets; and (c) calculating an average level of each target in the droplets based on the R signals and without determining which of the at least two targets for each signal amplified in individual amplification-positive droplets for such signal. For example, if T denotes the number of targets, then $T>R$.

F2. The method of paragraph F1, further comprising a step of determining a total number of droplets that are amplification-positive for any of the at least two targets reported on by each signal, and wherein the step of calculating is based on the total number determined for each of the R signals.

F3. The method of paragraph F1 or F2, wherein the step of calculating includes a step of finding solutions to a set of simultaneous equations.

G1. A composition, comprising: a droplet containing a probe, the probe including an oligonucleotide, a first fluorophore, a second fluorophore, and an energy transfer moiety, wherein the energy transfer moiety is a quencher and/or an energy transfer partner for one or both of the first and second fluorophores.

G2. The composition of paragraph G1, wherein the first fluorophore, the second fluorophore, and the energy transfer moiety are each covalently attached to the oligonucleotide.

G3. The composition of paragraph G1 or G2, further comprising a plurality of droplets containing the probe and disposed in a carrier fluid.

G4. The composition of any of paragraphs G1 to G3, wherein the droplet contains a template molecule and amplification reagents capable of amplifying at least a region of the template molecule, and wherein the probe is capable of binding to amplicons generated by amplification of the region of the template molecule.

G5. The composition of any of paragraphs G1 to G4, wherein the probe is a first probe, and wherein the droplet further comprises a second probe including the first fluorophore or the second fluorophore, but not both the first fluorophore and the second fluorophore.

G6. The composition of any of paragraphs G1 to G5, wherein the energy transfer moiety is a quencher attached to a nucleotide at the 5'-end of the oligonucleotide.

G7. The composition of any of paragraphs G1 to G6, wherein each of the first fluorophore, the second fluorophore, and the energy transfer moiety is attached to a different nucleotide of the oligonucleotide.

G8. The composition of paragraph G7, wherein a pair of the first fluorophore, the second fluorophore, and the energy transfer moiety are attached to the same nucleotide of the oligonucleotide.

G9. The composition of any of paragraphs G1 to G8, wherein at least one of the first fluorophore, the second fluorophore, and the energy transfer moiety is attached to a nucleotide of the oligonucleotide via another of the first fluorophore, the second fluorophore, and the energy transfer moiety.

G10. The composition of any of paragraphs G1 to G9, wherein a fluorophore or a quencher is attached to the 5'-end of the oligonucleotide, wherein a fluorophore or a quencher is attached to the 3'-end of the oligonucleotide, and wherein a fluorophore or a quencher is attached to a nucleotide intermediate the 5'-end and the 3'-end.

G11. The composition of any of paragraphs G1 to G10, wherein one or more of the first fluorophore, the second fluorophore, and the energy transfer moiety are attached to one or more internal nucleotides disposed intermediate the 5'-end and the 3'-end of the oligonucleotide.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a multiplexed digital amplification assay, the method comprising:
  amplifying more than R targets in partitions;
  creating R signals representative of light detected in R different wavelength regimes from the partitions, where $R \geq 2$; and
  calculating an average level of each target in the partitions based on the R signals, wherein the level calculated accounts for a coincidence of all possible combinations of the more than R targets in the same individual partitions;
  wherein the more than R targets include three targets, and wherein the average levels of the three targets are calculated based on light detected from only two fluorophores associated with probes that bind to amplicons of the three targets during amplification.

2. The method of claim 1, wherein amplification of each target of the more than R targets is reported by a different signal or combination of the signals than any of the other more than R targets individually.

3. The method of claim 1, wherein each of the signals reports amplification of a different combination of at least two of the more than R targets.

4. The method of claim 3, wherein the partitions are droplets, further comprising a step of determining a number of droplets exhibiting amplification of any of the at least two targets for each signal, and wherein the step of calculating is based on the number determined for each of the R signals.

5. The method of claim 1, wherein the two fluorophores are VIC and FAM.

6. The method of claim 5, wherein the partitions contain a first probe for a first of the three targets, a second probe for a second of the three targets, and a third probe for a third of the three targets, and wherein the first probe is labeled exclusively with VIC, the second probe is labeled exclusively with FAM, and the third probe is labeled with both VIC and FAM.

7. The method of claim 6, wherein the third probe includes a FAM-labeled probe that is not labeled with VIC and a VIC-labeled probe that is not labeled with FAM.

8. The method of claim 1, wherein the average level is a concentration.

9. The method of claim 1, wherein the step of calculating an average level includes a step of determining a total number of amplification-positive partitions for each type of the more than R targets and a step of determining a total number of partitions.

10. The method of claim 1, further comprising a step of distributing copies of the more than R targets among the partitions such that some partitions contain more than one copy of a given target.

11. The method of claim 1, wherein there are at least four targets.

12. A method of performing a multiplexed digital amplification assay, the method comprising:
  amplifying targets in partitions;
  detecting light from the partitions; and
  calculating levels of at least three of the targets based on light detected from only two fluorophores, wherein the levels calculated account for a coincidence of all possible combinations of the at least three targets in the same individual partitions.

13. The method of claim 12, wherein the partitions contain a first probe for a first target of the at least three targets, a second probe for a second target of the at least three targets, and a third probe for a third target of the at least three targets, and wherein the first probe is labeled exclusively with a first fluorophore, the second probe is labeled exclusively with a second fluorophore, and the third probe is labeled with the first fluorophore and the second fluorophore.

14. The method of claim 13, wherein the third probe includes a probe labeled with the first fluorophore and not the second fluorophore and another probe labeled with the second fluorophore and not the first fluorophore.

15. The method of claim 13, wherein the first fluorophore is VIC and the second fluorophore is FAM.

* * * * *